United States Patent
Yamada et al.

(10) Patent No.: US 11,742,105 B2
(45) Date of Patent: Aug. 29, 2023

(54) SCANNING MAGNET AND PARTICLE THERAPY SYSTEM

(71) Applicant: Hitachi, Ltd., Tokyo (JP)

(72) Inventors: Takahiro Yamada, Tokyo (JP); Takuya Nomura, Tokyo (JP); Seiji Soeda, Tokyo (JP)

(73) Assignee: HITACHI, LTD., Tokyo (JP)

(*) Notice: Subject to any disclaimer, the term of this patent is extended or adjusted under 35 U.S.C. 154(b) by 111 days.

(21) Appl. No.: 17/603,381

(22) PCT Filed: Jun. 30, 2020

(86) PCT No.: PCT/JP2020/025639
§ 371 (c)(1),
(2) Date: Oct. 13, 2021

(87) PCT Pub. No.: WO2021/020004
PCT Pub. Date: Feb. 4, 2021

(65) Prior Publication Data
US 2022/0181042 A1   Jun. 9, 2022

(30) Foreign Application Priority Data
Jul. 26, 2019   (JP) .................................. 2019-137421

(51) Int. Cl.
*G21K 1/093* (2006.01)
*A61N 5/10* (2006.01)
*H01F 7/20* (2006.01)
*H01F 27/28* (2006.01)
*H05H 7/04* (2006.01)

(52) U.S. Cl.
CPC ............ *G21K 1/093* (2013.01); *A61N 5/1078* (2013.01); *H01F 7/20* (2013.01); *H01F 27/28* (2013.01);

(Continued)

(58) Field of Classification Search
CPC ........ G21K 1/093; G21K 5/04; A61N 5/1078; A61N 2005/1087; A61N 5/1043;
(Continued)

(56) References Cited

U.S. PATENT DOCUMENTS 8,378,312 B1   2/2013  Gordon et al.
10,548,212 B2 * 1/2020  Aoki ...................... H05H 13/04
(Continued)

FOREIGN PATENT DOCUMENTS

JP   05-264797 A   10/1993
JP   10-300899 A   11/1998
(Continued)

OTHER PUBLICATIONS

International Search Report of PCT/JP2020/025639 dated Sep. 15, 2020.

*Primary Examiner* — David A Vanore
(74) *Attorney, Agent, or Firm* — Mattingly & Malur, PC

(57) ABSTRACT

A scanning magnet that deflects a charged particle beam has a winding U provided with grooves SL1 and SL4 provided at facing positions. A passing direction of a conductive wire forming the winding U passes through the groove SL1 in a γ-axis positive direction, and passes through the groove SL4 in a γ-axis negative direction. The winding U has a loop path SL1-SL4 in which the groove SL1 is directed to the γ-axis positive direction, and the groove SL4 is directed to the γ-axis negative direction. When a current flows in the γ-axis positive direction in a winding section U+ disposed in the groove SL1, a current flows in the γ-axis negative direction in a winding section U− disposed in the groove SL4. A yoke, the winding U, a winding V, and a winding W have a 120° rotationally symmetric structure with respect to a central axis of the yoke.

13 Claims, 19 Drawing Sheets

| (1) | (2) | (3) | (4) | (5) | (6) |
|-----|-----|-----|-----|-----|-----|
| U+  | W−  | V+  | U−  | W+  | V−  |

(52) U.S. Cl.
CPC ....... *H05H 7/04* (2013.01); *A61N 2005/1087* (2013.01); *H05H 2007/048* (2013.01); *H05H 2277/11* (2013.01)

(58) Field of Classification Search
CPC .................. A61N 5/1001; A61N 5/103; A61N 2005/1085; H01F 7/20; H01F 27/28; H01F 7/06; H01F 27/306; H05H 7/04; H05H 2007/048; H05H 2277/11
See application file for complete search history.

(56) References Cited

U.S. PATENT DOCUMENTS

| | | | | |
|---|---|---|---|---|
| 11,026,320 | B1 * | 6/2021 | Furukawa | H05H 7/001 |
| 2003/0183779 | A1 * | 10/2003 | Norimine | G21K 5/04 250/398 |
| 2009/0218506 | A1 * | 9/2009 | Nakasuji | H01J 37/26 250/492.3 |
| 2017/0229281 | A1 * | 8/2017 | Furukawa | G21K 5/04 |
| 2017/0339778 | A1 * | 11/2017 | Aoki | H05H 7/10 |
| 2019/0255357 | A1 | 8/2019 | Takayama et al. | |
| 2019/0329070 | A1 * | 10/2019 | Nakashima | H05H 7/04 |

FOREIGN PATENT DOCUMENTS

| | | |
|---|---|---|
| JP | 2007-260222 A | 10/2007 |
| JP | 2013-206635 A | 10/2013 |
| JP | 2016-083344 A | 5/2016 |
| JP | 2019-034108 A | 3/2019 |
| JP | 2020-041971 A | 3/2020 |

* cited by examiner

θ : SCAN ANGLE
ψ : KICK ANGLE
r : KICK AMOUNT

| | (1) | (2) | (3) | (4) | (5) | (6) |
|---|---|---|---|---|---|---|
| | U+ | W- | V+ | U- | W+ | V- |

FIG. 5

| IRRADIATION POSITION | | EXCITATION CURRENT TARGET VALUE | | |
|---|---|---|---|---|
| X | Y | Iu* | Iv* | Iw* |
| X1 | Y1 | Iu_1_1 | Iv_1_1 | Iw_1_1 |
| X2 | Y1 | Iu_2_1 | Iv_2_1 | Iw_2_1 |
| ⋮ | ⋮ | ⋮ | ⋮ | ⋮ |
| Xp | Yq | Iu_p_q | Iv_p_q | Iw_p_q |

| | (1) | (2) | (3) | (4) | (5) | (6) | (7) | (8) | (9) | (10) | (11) | (12) |
|---|---|---|---|---|---|---|---|---|---|---|---|---|
| INNER SIDE | U+ | U+ | W- | W- | V+ | V+ | U- | U- | W+ | W+ | V- | V- |
| OUTER SIDE | U+ | U+ | W- | W- | V+ | V+ | U- | U- | W+ | W+ | V- | V- |

| | (1) | (2) | (3) | (4) | (5) | (6) | (7) | (8) | (9) | (10) | (11) | (12) |
|---|---|---|---|---|---|---|---|---|---|---|---|---|
| INNER SIDE | U+ | U+ | W- | W- | V+ | V+ | U- | U- | W+ | W+ | V- | V- |
| OUTER SIDE | U+ | W- | W- | V+ | V+ | U- | U- | W+ | W+ | V- | V- | U+ |

SCANNING MAGNET AND PARTICLE THERAPY SYSTEM

TECHNICAL FIELD

The present invention relates to a scanning magnet and a particle therapy system, and particularly, to a technique for scanning a charged particle beam with which a patient is irradiated.

BACKGROUND ART

Particle therapy in which a target volume is irradiated with a charged particle beam such as a proton beam or a carbon ion beam has been widely performed. In a particle therapy system that performs particle therapy, a charged particle beam based on charged particles accelerated to have necessary energy by an accelerator is transported up to an irradiation nozzle by a transport device, and a target volume is irradiated with the charged particle beam from the irradiation nozzle.

In the particle therapy, scanning irradiation of irradiating the target volume while changing the irradiation position of the charged particle beam may be performed. In the scanning irradiation, the depth of the irradiation position of the charged particle beam is changed by changing the energy of the charged particle beam. In addition, the irradiation position in a plane perpendicular to a depth direction is changed by generating a magnetic field in a direction crossing the charged particle beam and deflecting the charged particle beam. Therefore, the accelerator is provided with a device that controls the energy of the charged particle beam, and the irradiation nozzle is provided with a scanning magnet that generates a magnetic field crossing the charged particle beam.

PTL 1 below discloses a cylindrical scanning magnet. A magnetic field in an X-axis direction and a Y-axis direction, that is, a bipolar magnetic field is generated on an XY plane crossing a longitudinal direction of the cylindrical shape. PTL 2 discloses an 8-pole scanning magnet capable of performing scanning in two directions in an XY plane. The scanning magnet has eight windings arranged at equal angular intervals in a circumferential direction surrounding the charged particle beam. A pair of windings facing each other is connected in series to the same power supply, and scanning in two directions is performed by adjusting currents flowing through four pairs of windings.

CITATION LIST

Patent Literature

PTL 1: JP 2013-206635 A
PTL 2: Specification of U.S. Pat. No. 8,378,312

SUMMARY OF INVENTION

Technical Problem

The scanning magnet in PTL 1 generates a magnetic field in one direction. Thus, in order to scan the charged particle beam in two directions on a plane crossing the particle beam, it is necessary to arrange two scanning magnets that generate magnetic fields in different directions, in a cascade manner. Thus, the irradiation nozzle becomes large. The scanning magnet on the downstream side needs to form a magnetic field generation region including the trajectory of the charged particle beam scanned by the scanning magnet on the upstream side. Thus, the scanning magnet on the downstream side becomes larger than the scanning magnet on the upstream side.

In the scanning magnet in PTL 2, scanning in two directions can be performed with one scanning magnet. However, due to inappropriate distribution of the magnetic field in a direction along the circumferential direction surrounding the charged particle beam, or the like, an error may occur in an angle at which the charged particle beam is deflected, depending on the irradiation position of the charged particle beam.

An object of the present invention is to reduce the size of a scanning magnet and reduce an error in an angle at which a charged particle beam is deflected.

Solution to Problem

The present invention includes a plurality of windings each having a forward section and a backward section extending along a trajectory of a charged particle beam, and the windings surrounding a columnar space through which the charged particle beam passes. The forward section and the backward section in each of the windings are arranged at a predetermined interval when viewed in an outer circumferential direction of the columnar space, and the forward section or the backward section of one of the plurality of windings is disposed between the forward section and the backward section of another winding.

Advantageous Effects of Invention

According to the present invention, it is possible to reduce the size of a scanning magnet and reduce an error in an angle at which a charged particle beam is deflected.

BRIEF DESCRIPTION OF DRAWINGS

FIG. 5 is a diagram illustrating an irradiation position/excitation current conversion table.

DESCRIPTION OF EMBODIMENTS

Scanning magnets according to embodiments of the present invention will be described below with reference to the drawings. The same reference signs are given to the same matters illustrated in a plurality of drawings, and repetitive description will be avoided.

Figure 1:
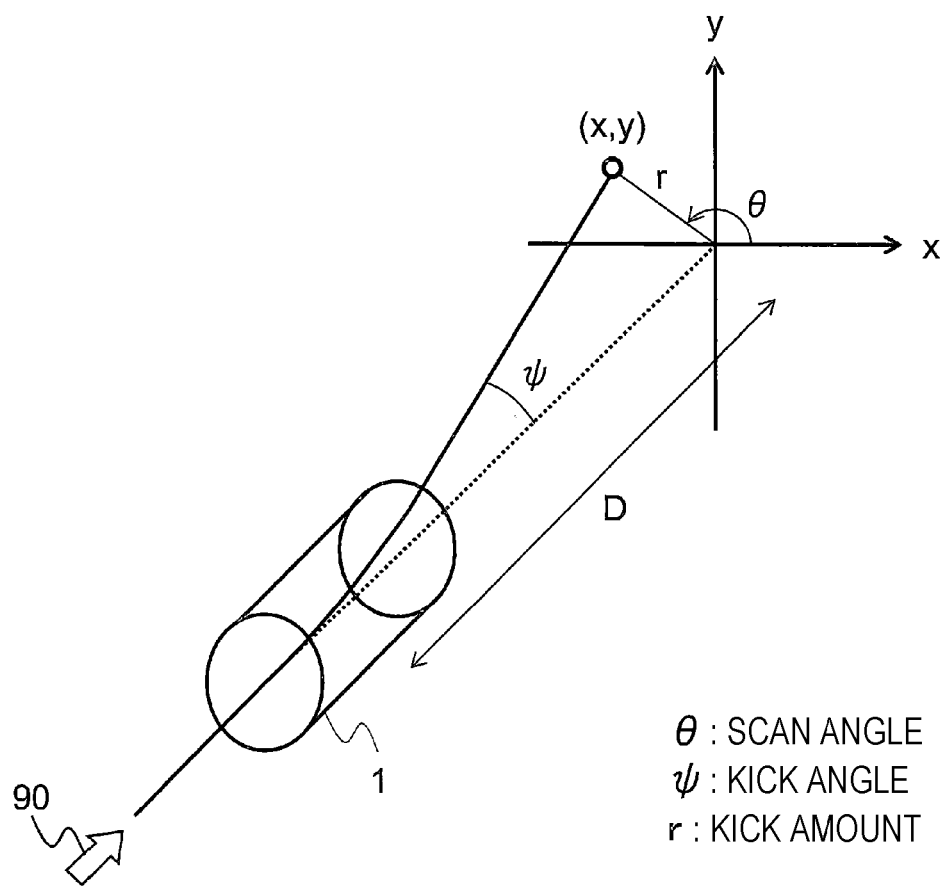
FIG. 1 is a diagram conceptually illustrating a scanning magnet and a charged particle beam.

FIG. 1 conceptually illustrates a scanning magnet 1 according to a first embodiment of the present invention and a charged particle beam 90 passing through the scanning magnet 1. The scanning magnet 1 has a tubular shape, and the charged particle beam 90 passes through an internal space (columnar space) surrounded by the scanning magnet 1. The scanning magnet 1 is provided with a plurality of windings. A magnetic field is generated in the internal space by the current flowing through each of the windings, and the charged particle beam is deflected. As will be described later, the direction of the charged particle beam is adjusted by adjusting the directions and the magnitudes of the magnetic fields generated from the plurality of windings. In the following description, the magnetic flux density [T] is used as a physical quantity quantitatively representing the magnetic field.

In FIG. 1, an xy orthogonal coordinate system having an isocenter being an irradiation center, as an origin, is defined. An intersection of an isocenter plane in which the isocenter exists and the trajectory of the charged particle beam 90 is defined as an irradiation position, and the irradiation position is represented by coordinate values (x, y) in xy orthogonal coordinate system. The distance from the origin to the irradiation position is defined as a kick amount r, and the angle of a direction from the origin to the irradiation position with respect to an x-axis is defined as a scan angle θ. The angle at which the charged particle beam 90 is deflected by the scanning magnet 1 is defined as a kick angle ψ.

The distance from a reference point in the scanning magnet 1 to the isocenter plane, that is, the xy plane is defined as D. The reference point in the scanning magnet 1 is determined, for example, to the center of gravity of the internal space.

Figures 2, 3:
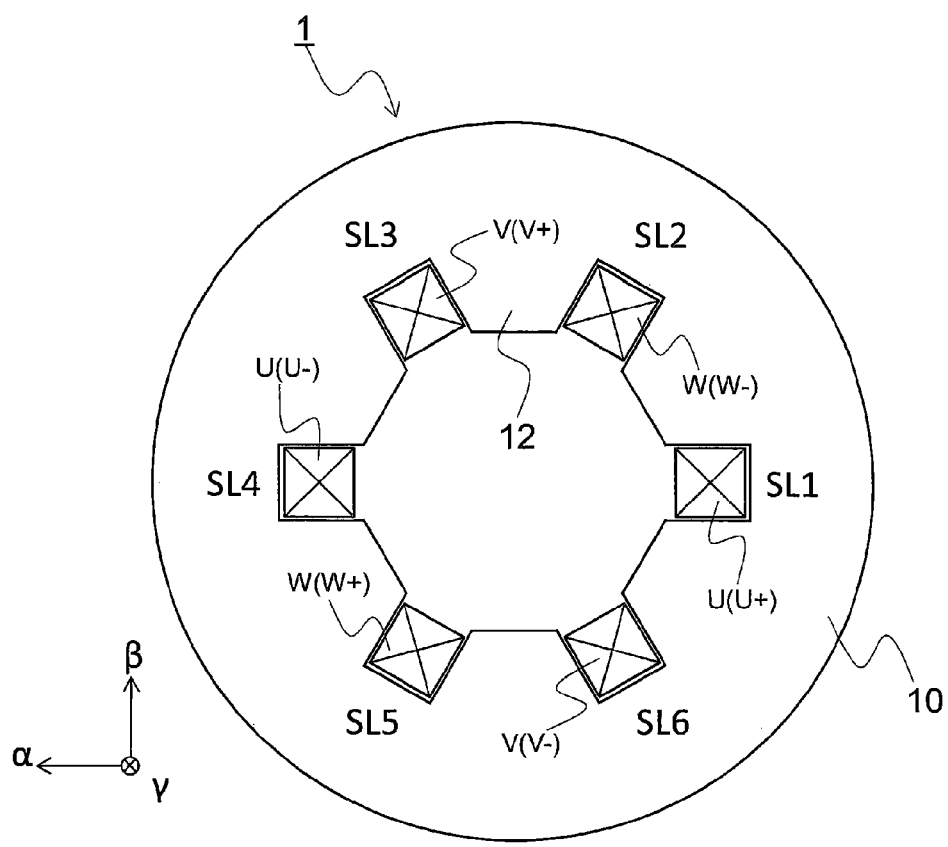
FIG. 2 is a diagram schematically illustrating a cross-sectional shape of the scanning magnet.
FIG. 3 is a diagram illustrating a correspondence relation between a groove and a winding section disposed in the groove.

FIG. 2 schematically illustrates a cross-sectional shape when the scanning magnet 1 is cut along a plane perpendicular to an axial direction and viewed from the upstream side of the trajectory of the charged particle beam 90. In FIG. 2, a direction in which the charged particle beam 90 is directed from the upstream side to the downstream side is defined as a γ-axis positive direction. The leftward direction and the upward direction in FIG. 2 are defined as an α-axis positive direction and a β-axis positive direction, respectively. The scanning magnet 1 includes a tubular yoke 10, and three systems of windings U, V, and W. The yoke 10 is made of a magnetic material such as iron.

Six grooves SL1 to SL6 are formed on the inner wall surface of the yoke 10 counterclockwise at 60° intervals in this order. The grooves SL1 to SL6 are recessed outward and extend in the axial direction (γ-axis direction). A tooth 12 is formed between the adjacent grooves. Each tooth 12 has a shape protruding to the inside of the yoke 10 with reference to the deepest portions of the grooves SL1 to SL6.

In the following description, an expression that the winding passes through the groove in the γ-axis positive direction or a γ-axis negative direction is made for convenience of describing the structure of the winding, and does not limit a method of arranging windings in the yoke 10. For example, a conductive wire that passes through the first groove in the γ-axis positive direction and passes through the second groove in the γ-axis negative direction has a loop structure of passing through the first groove and then passing through the second groove. Such a loop structure may not necessarily be manufactured by causing a conductive wire to pass through the first groove and pass through the second groove.

The winding U is provided in the grooves SL1 and SL4 provided at facing positions. When a passing direction of a conductive wire forming the winding U is defined such that the conductive wire passes through the groove SL1 in the γ-axis positive direction, the conductive wire forming the winding U passes through the groove SL4 in the γ-axis negative direction. That is, the conductive wire forming the winding U winds around a loop path SL1-SL4 in which the groove SL1 is directed to the γ-axis positive direction, and the groove SL4 is directed to the γ-axis negative direction.

The conductive wire forming the winding U may pass through the grooves SL1 and SL4 only once, or may alternately pass through the grooves SL1 and SL4 a plurality of times. That is, the conducting wire forming the winding U may make one turn or a plurality of turns in the loop path SL1-SL4. When a current flows in the γ-axis positive direction in a winding section U+ disposed in the groove SL1, a current flows in the γ-axis negative direction in a winding section U− disposed in the groove SL4.

The winding V is provided in the grooves SL3 and SL6 provided at facing positions. When a passing direction of a conductive wire forming the winding V is defined such that the conductive wire passes through the groove SL3 in the γ-axis positive direction, the conductive wire forming the winding V passes through the groove SL6 in the γ-axis negative direction. That is, the conductive wire forming the winding V winds around a loop path SL3-SL6 in which the groove SL3 is directed to the γ-axis positive direction, and the groove SL6 is directed to the γ-axis negative direction.

The conductive wire forming the winding V may pass through the grooves SL3 and SL6 only once, or may alternately pass through the grooves SL3 and SL6 a plurality of times. That is, the conducting wire forming the winding V may make one turn or a plurality of turns in the loop path SL3-SL6. When a current flows in the γ-axis positive direction in a winding section V+ disposed in the groove SL3, a current flows in the γ-axis negative direction in a winding section V− disposed in the groove SL6.

The winding W is provided in the grooves SL5 and SL2 provided at facing positions. When a passing direction of a conductive wire forming the winding W is defined such that the conductive wire passes through the groove SL5 in the γ-axis positive direction, the conductive wire forming the winding W passes through the groove SL2 in the γ-axis negative direction. That is, the conductive wire forming the winding W winds around a loop path SL5-SL2 in which the groove SL5 is directed to the γ-axis positive direction, and the groove SL2 is directed to the γ-axis negative direction.

The conductive wire forming the winding W may pass through the grooves SL5 and SL2 only once, or may alternately pass through the grooves SL5 and SL2 a plurality of times. That is, the conducting wire forming the winding W may make one turn or a plurality of turns in the loop path SL5-SL2. When a current flows in the γ-axis positive direction in a winding section W+ disposed in the groove SL5, a current flows in the γ-axis negative direction in a winding section W− disposed in the groove SL2.

FIG. 3 illustrates the arrangement of the winding sections U+, U−, V+, V−, W+, and W− in the grooves SL1 to SL6. Symbols "(1)" to "(6)" indicate the grooves SL1 to SL6, respectively. As illustrated in FIG. 3, the winding sections U+, W−, V+, U−, W+, and V− are arranged in the grooves SL1 to SL6, respectively.

In the following description, among both ends of the winding U, one end into which a current flows when the current in the γ-axis positive direction flows in the winding section U+ is defined as a start end, and the other end from which the current flows out is defined as a terminal end. Among both ends of the winding V, one end into which a current flows when the current in the γ-axis positive direction flows in the winding section V+ is defined as a start end, and the other end from which the current flows out is defined as a terminal end. Among both ends of the winding W, one end into which a current flows when the current in the γ-axis positive direction flows in the winding section W+ is defined as a start end, and the other end from which the current flows out is defined as a terminal end.

The winding sections U+, V+, and W+ through which the current flows in the γ-axis positive direction when the current flows from the start end are defined as forward sections. The winding sections U−, V−, and W− through which the current flows in the γ-axis negative direction when the current flows from the start end are defined as backward sections. That is, the forward sections of the windings U, V, and W are disposed in the grooves SL1, SL3, and SL5, respectively, and the backward sections of the windings U, V, and W are disposed in the grooves SL2, SL4, and SL6, respectively.

A coil end conductive wire connecting the forward section and the backward section of each winding is disposed at the end portion of the scanning magnet 1 so as not to interfere with other windings with a small influence on the trajectory of the charged particle beam 90.

The terms "forward section" and "backward section" are used for convenience of describing the structure of the winding, and do not limit the direction of the current flowing through each winding. The current flowing through each winding is controlled by a scanning magnet control apparatus described later.

As described above, each of the winding U, the winding V, and the winding W includes the forward section and the backward section extending along the axial direction (γ-axis direction) of the scanning magnet 1, that is, along the trajectory of the charged particle beam. The forward section and the backward section included in each winding are arranged at 180° when viewed in the outer circumferential direction of the columnar space surrounded by the yoke 10. The forward section of one winding and the backward section of another winding are disposed between the forward section and the backward section of the other winding among the winding U, the winding V, and the winding W.

The yoke 10, the winding U, the winding V, and the winding W have a 120° rotationally symmetric structure with respect to the central axis of the yoke 10. That is, the winding U, the winding V, and the winding W have a 120° rotationally symmetric structure around an axis of the columnar space surrounded by the yoke 10.

By causing DC excitation currents Iu=Iu*, Iv=Iv*, and Iw=Iw* represented by the following (Equation 1) to (Equation 3) to flow in the winding U, the winding V, and the winding W, respectively, magnetic flux density BL(I) that deflects the charged particle beam 90 in a direction represented by the scan angle θ and the kick angle ψ (I) is generated in the internal space of the yoke 10.

$$Iu^* = I \cdot \sin \theta \qquad \text{(Equation 1)}$$

$$Iv^* = I \cdot \sin(\theta - 2\pi/3) \qquad \text{(Equation 2)}$$

$$Iw^* = I \cdot \sin(\theta - 4\pi/3) \qquad \text{(Equation 3)}$$

(Equation 1) to (Equation 3) are three sine functions that have the scan angle θ as an angle variable and are shifted from each other by 120° on an angle variable axis. The magnetic flux density BL(I) is magnetic flux density perpendicular to the γ-axis, and is represented by an increasing function with respect to a current coefficient I. That is, the magnetic flux density BL(I) increases as the current coefficient I increases. (Equation 1) to (Equation 3) may be expressed by a cosine function instead of the sine function. (Equation 1) to (Equation 3) may be expressed by a function obtained by shifting the sine function or the cosine function by a predetermined value on the angle variable axis.

Assuming that the magnetic rigidity of the charged particle beam 90 is Bρ, the kick angle ψ(I) is represented as (Equation 4).

$$\psi(I) = \arctan[BL(I)/B\rho] \approx BL(I)/B\rho \qquad \text{(Equation 4)}$$

Thus, the kick amount r is represented by (Equation 5) using the distance D from the reference point of the scanning magnet 1 to the isocenter plane.

$$r = D \cdot \tan[\psi(I)] = D \cdot BL(I)/B\rho \qquad \text{(Equation 5)}$$

Therefore, the scanning magnet control apparatus performs control processing as follows. That is, the scanning magnet control apparatus obtains the target values Iu*, Iv*, and Iw* of the excitation currents to flow through the respective windings U, V, and W by designating the kick angle ψ and the scan angle θ.

The scanning magnet control apparatus controls drive circuits of the winding U, the winding V, and the winding W so that the excitation currents Iu, Iv, and Iw flowing through the winding U, the winding V, and the winding W approach or coincide with the excitation current target values Iu*, Iv*, and Iw*. Thus, the charged particle beam 90 is directed in a direction determined by the kick angle ψ and the scan angle θ.

Figure 4:
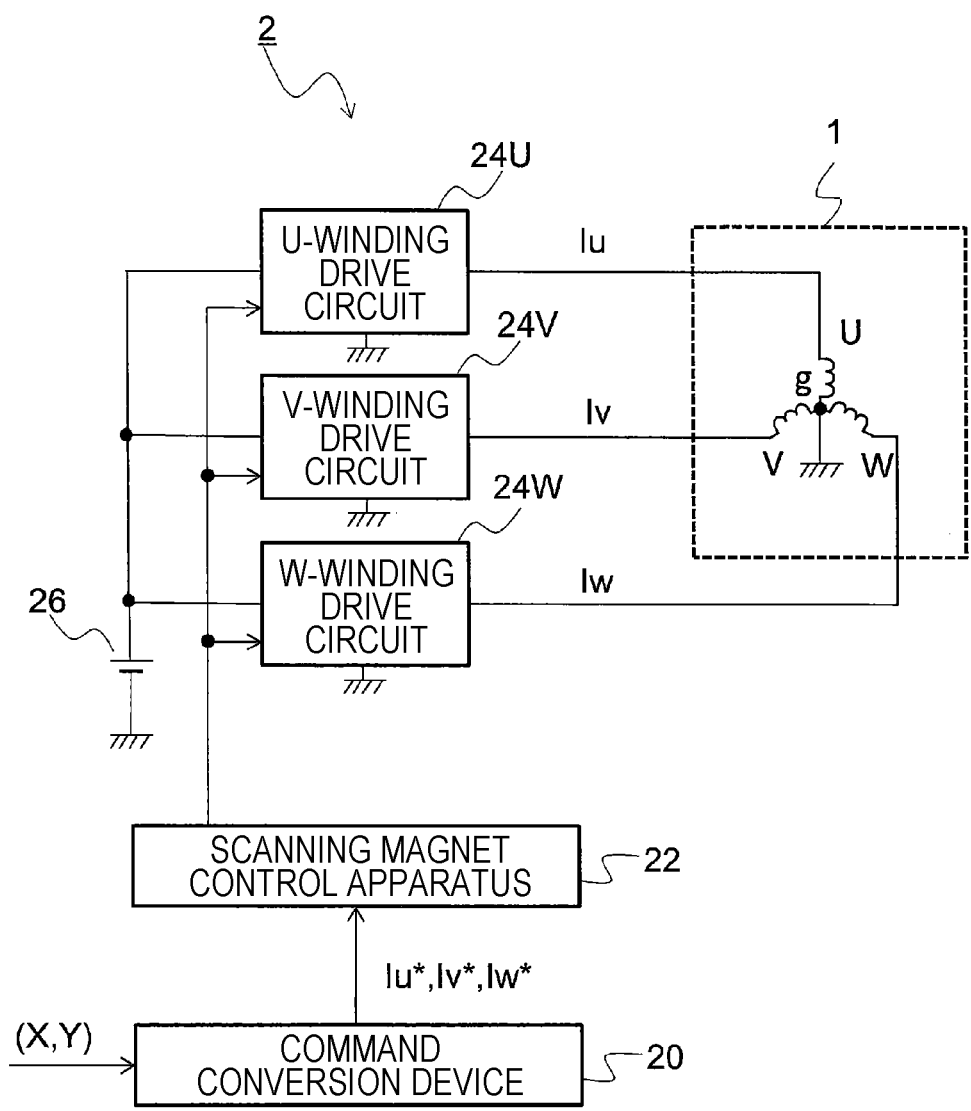
FIG. 4 is a diagram illustrating a scanning magnet control system.

FIG. 4 illustrates a scanning magnet control system 2. The scanning magnet control system 2 includes a DC power source 26, a U-winding drive circuit 24U, a V-winding drive circuit 24V, a W-winding drive circuit 24W, a scanning magnet control apparatus 22, and a command conversion device 20. The terminal ends of the winding U, the winding V, and the winding W of the scanning magnet 1 are connected to a neutral point g. The neutral point g is connected to a ground conductor.

A negative electrode terminal of the DC power source 26 is connected to the ground conductor. A positive electrode terminal is connected to the U-winding drive circuit 24U, the V-winding drive circuit 24V, and the W-winding drive circuit 24W. The U-winding drive circuit 24U, the V-winding drive circuit 24V, and the W-winding drive circuit 24W are connected to the start end of the winding U, the start end of the winding V, and the start end of the winding W, respectively. The U-winding drive circuit 24U, the V-winding drive circuit 24V, and the W-winding drive circuit 24W are connected to the ground conductor.

The scanning magnet control apparatus 22 and the command conversion device 20 may include a processor. The scanning magnet control apparatus 22 may further include a digital circuit. The processor constituting the scanning magnet control apparatus 22 controls the digital circuit by executing a program stored in a memory in the scanning magnet control system 2 or a program read from the outside. The U-winding drive circuit 24U, the V-winding drive circuit 24V, and the W-winding drive circuit 24W are controlled by the digital circuit.

The command conversion device 20 may store an irradiation position/excitation current conversion table illustrated in FIG. 5. The irradiation position/excitation current conversion table is a table in which the xy coordinate values (X, Y) of the irradiation position are associated with the excitation current target values Iu*, Iv*, and Iw*. FIG. 5 illustrates a table when p irradiation positions in the x-axis direction and q irradiation positions in the γ-axis direction (X1, Y1), . . . (Xp, Y1), . . . and (Xp, Yq) are determined.

That is, FIG. 5 illustrates an example in which (Iu_11, Iv_11, Iw_11), . . . (Iu_p1, Iv_p1, Iw_p1), . . . and (Iu_pq, Iv_pq, Iw_pq) are associated with the irradiation position using the excitation current target values Iu*, Iv*, and Iw*.

The irradiation position/excitation current table is obtained in advance by performing the following steps (i) to (iv). (i) step of converting the xy coordinate values (X, Y) into rθ coordinate values (r, θ), (ii) step of obtaining the kick angle ψ(I) based on the kick amount r and further obtaining the current coefficient I, (iii) step of applying the current coefficient I and the scan angle θ to (Equation 1) to (Equation 3) to obtain the excitation current target values Iu*, Iv*, and Iw*, and (iv) step of associating the xy coordinate values (X, Y) with the excitation current target values Iu*, Iv*, and Iw*.

The command conversion device 20 refers to the irradiation position/excitation current conversion table to obtain the excitation current target values Iu*, Iv*, and Iw* corresponding to the xy coordinate values (X, Y) of the irradiation position, and output the obtained excitation current target values Iu*, Iv*, and Iw* to the scanning magnet control apparatus 22. The scanning magnet control apparatus 22 controls the U-winding drive circuit 24U, the V-winding drive circuit 24V, and the W-winding drive circuit 24W so that the excitation currents Iu, Iv, and Iw approach or coincide with the excitation current target values Iu*, Iv*, and Iw*, respectively.

The U-winding drive circuit 24U, the V-winding drive circuit 24V, and the W-winding drive circuit 24W apply an excitation current to the winding U, the winding V, and the winding W based on the power output from the DC power source 26 under the control of the scanning magnet control apparatus 22.

The command conversion device 20 may obtain the excitation current target values Iu*, Iv*, and Iw* by arithmetic processing regardless of the irradiation position/excitation current conversion table. In this case, the command conversion device 20 performs the above steps (i) to (iii) by the arithmetic processing of the processor, to obtain the excitation current target values Iu*, Iv*, and Iw*.

Figure 6:
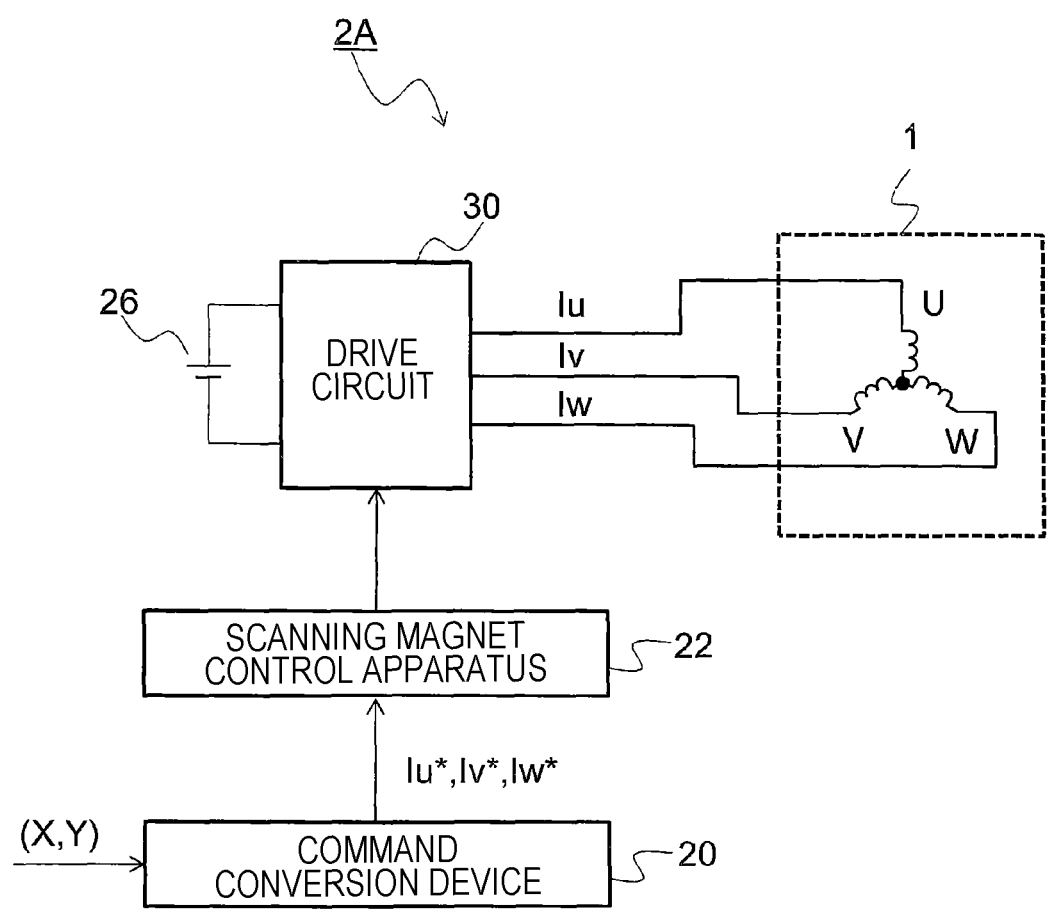
FIG. 6 is a diagram illustrating the scanning magnet control system.

FIG. 4 illustrates an embodiment in which the terminal ends of the winding U, the winding V, and the winding W are connected to the ground conductor, and the DC power source 26, the U-winding drive circuit 24U, the V-winding drive circuit 24V, and the W-winding drive circuit 24W are also connected to the ground conductor. The terminal ends of the winding U, the winding V, and the winding W may not be connected to the ground conductor. FIG. 6 illustrates a scanning magnet control system 2A when the terminal ends of the winding U, the winding V, and the winding W are not connected to the ground conductor.

The scanning magnet control system 2A includes a DC power source 26, a drive circuit 30, a scanning magnet control apparatus 22, and a command conversion device 20. Both ends of the DC power source 26 are connected to the drive circuit 30. The drive circuit 30 is connected to the start end of the winding U, the start end of the winding V, and the start end of the winding W.

The scanning magnet control apparatus 22 controls the drive circuit 30 so that the excitation current Iu flowing through the winding U, the excitation current Iv flowing through the winding V, and the excitation current Iw flowing through the winding W approach or coincide with the excitation current target values Iu*, Iv*, and Iw*, respectively. The drive circuit 30 causes the excitation current to flow in the winding U, the winding V, and the winding W based on the power output from the DC power source 26 under the control of the scanning magnet control apparatus 22.

FIGS. 4 and 6 illustrate a configuration in which the terminal ends of the winding U, the winding V, and the winding W are commonly connected, and the winding U, the winding V, and the winding W are star-connected. The winding U, the winding V, and the winding W may be delta-connected. In the delta connection, the terminal end of the winding U is connected to the start end of the winding V, the terminal end of the winding V is connected to the start end of the winding W, and the terminal end of the winding W is connected to the start end of the winding U. The start end of the winding U, the start end of the winding V, and the start end of the winding W, which are star-connected, correspond to a connection point of the winding W and the winding U, a connection point of the winding U and the winding V, and a connection point of the winding V and the winding W, respectively, in the delta connection.

Figure 7:
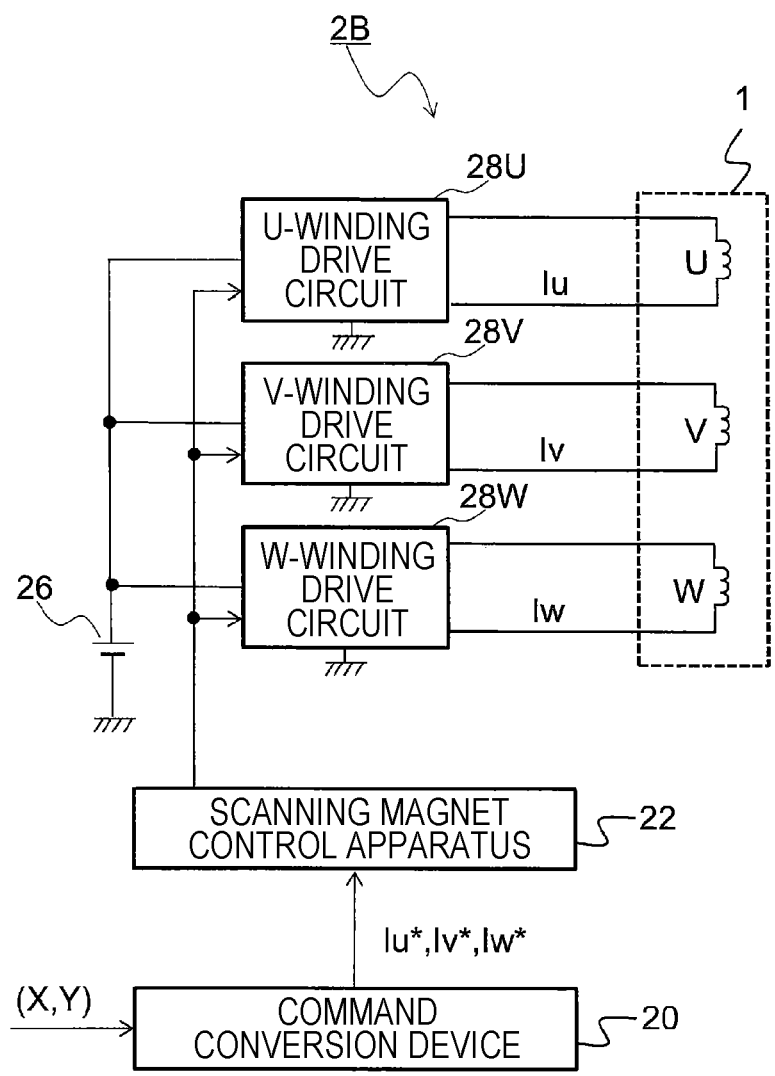
FIG. 7 is a diagram illustrating a scanning magnet control system.

The terminal ends of the winding U, the winding V, and the winding W may not be connected to the neutral point g. FIG. 7 illustrates a scanning magnet control system 2B in this case. Both ends of the winding U are connected to a U-winding drive circuit 28U. Both ends of the winding V are connected to a V-winding drive circuit 28V. Both ends of the winding W are connected to a W-winding drive circuit 28W. The U-winding drive circuit 28U, the V-winding drive circuit 28V, and the W-winding drive circuit 28W adjust currents flowing through the winding U, the winding V, and the winding W under the control of the scanning magnet control apparatus 22, respectively.

As described above, the scanning magnet 1 according to the present embodiment includes the winding U, the winding V, and the winding W surrounding the columnar space through which the charged particle beam passes, each of the windings having the forward section and the backward section extending along the trajectory of the charged particle beam. The forward section and the backward section in each winding (U, V, W) are arranged at a predetermined interval (180° in the above embodiment) when viewed in the outer circumferential direction of the columnar space. The forward section or the backward section of one winding among the winding U, the winding V, and the winding W are disposed between the forward section and the backward section of another winding.

The distribution of the magnetomotive force generated in the columnar space in a manner that DC excitation currents represented by (Equation 1) to (Equation 3) respectively flow in the winding U, the winding V, and the winding W in a state where each winding (U, V, W) has such a distributed winding structure is as follows. That is, when the outer circumferential direction of the columnar space is taken on a horizontal axis and the magnetomotive force is taken on a vertical axis, the distribution of the magnetomotive force becomes distribution approximate to a sine wave.

Thus, the flatness of the magnetic flux density when observed in a direction crossing magnetic force lines. Here, the flatness is defined as, for example, a width of a range in which the fluctuation of the magnetic flux density when observed in the direction crossing the magnetic force lines is within a predetermined range. When the columnar space has a cylindrical shape, the flatness may be defined as a range (length in a radial direction) in which the fluctuation of the magnetic flux density in the radial direction perpendicular to the magnetic force line is within a predetermined range. By improving the flatness of the magnetic flux density, a change in the beam width after the charged particle beam passes through the scanning magnet is suppressed.

Since the distribution of the magnetomotive force in the circumferential direction for all scan angles $\theta$ is distribution approximate to a sine wave, the change in the flatness with respect to the change in the scan angle $\theta$ is suppressed. Thus, variations in the kick angle and the kick amount of the charged particle beam due to the difference in the scan angle $\theta$ are suppressed.

The command conversion device 20 may output excitation current target values $Iu^*\_O$, $Iv^*\_O$, and $Iw^*\_O$ according to the following (Equation 6) to (Equation 8), to the scanning magnet control apparatus 22. The excitation current target values $Iu^*\_O$, $Iv^*\_O$, and $Iw^*\_O$ are values obtained by adding offset values $\Delta Iu$, $\Delta Iv$, and $\Delta Iw$ to the excitation current target values $Iu^*$, $Iv^*$, and $Iw^*$ represented by (Equation 1) to (Equation 3), respectively. The offset values $\Delta Iu$, $\Delta Iv$, and $\Delta Iw$ may be functions having the scan angle $\theta$ as a variable. The offset value is determined by experiment, simulation, or the like so that the flatness of the magnetic flux density in the internal space surrounded by the scanning magnet 1 is improved.

$$Iu^*\_O = I \cdot \sin\theta + \Delta Iu \quad \text{(Equation 6)}$$

$$Iv^*\_O = I \cdot \sin(\theta - 2\pi/3) + \Delta Iv \quad \text{(Equation 7)}$$

$$Iw^*\_O = I \cdot \sin(\theta - 4\pi/3) + \Delta Iw \quad \text{(Equation 8)}$$

Figure 8:
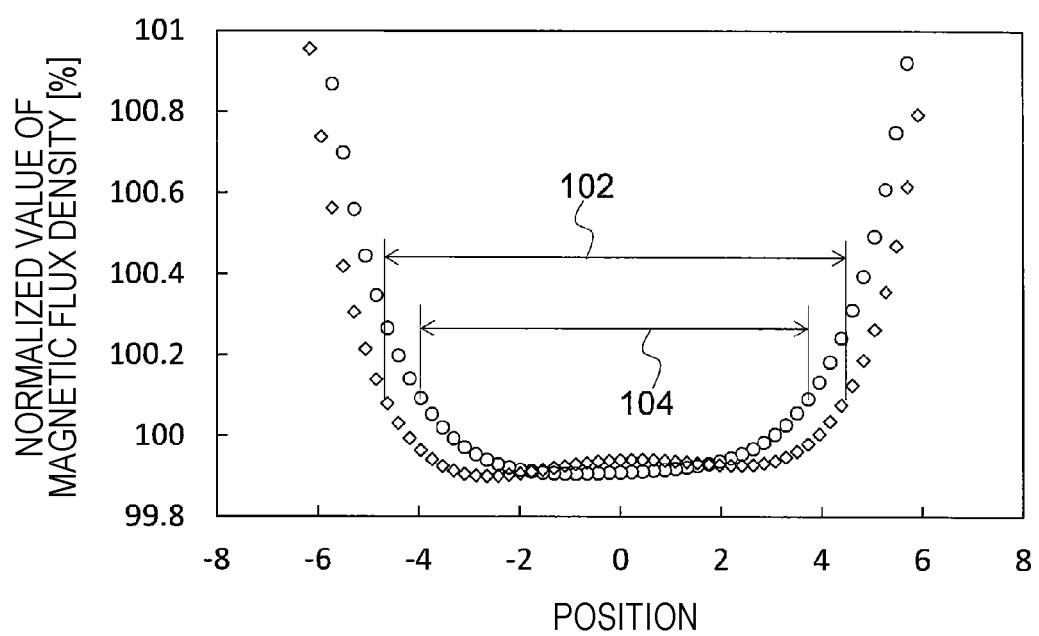
FIG. 8 is a diagram illustrating distribution of magnetic flux density.

Since the excitation currents flowing through the winding U, the winding V, and the winding W approach or coincide with the excitation current target values to which the offset values are added, the flatness of the magnetic flux density in the internal space of the scanning magnet 1 is improved, and the change in the flatness with respect to the change in the scan angle $\theta$ is suppressed. FIG. 8 illustrates the distribution of the magnetic flux density when the offset value $\Delta Iu$ is set to a negative value having a magnitude of 2.5% of the current coefficient I with respect to the scan angle $\theta = 0°$, that is, when $\Delta Iu$ is set to $-0.025I$.

The horizontal axis indicates a position on a straight line crossing the central axis of the yoke 10 in the radial direction. The vertical axis indicates a normalized value of the magnetic flux density when a certain reference value is set to 100%. A circle indicates the magnetic flux density when the offset values $\Delta Iu$, $\Delta Iv$, and $\Delta Iw$ are all set to 0. A rhombus indicates the magnetic flux density when the offset value $\Delta Iu$ is set to $-0.025I$ and both the offset values $\Delta Iv$ and $\Delta Iw$ are set to 0. The arrows 102 and 104 indicate a flat region in which the fluctuation of the magnetic flux density is within $\pm 0.1\%$, and the length of this flat region indicates the flatness. In FIG. 8, it is recognized that the flat region is longer and the flatness is better when the offset value $\Delta Iu$ is set to $-0.025I$ than when each offset value is set to 0.

As described above, the excitation current target values for the winding U, the winding V, and the winding W may be a trigonometric function having the scan angle $\theta$ as an angle variable, as shown in (Equation 1) to (Equation 3). As shown in (Equation 6) to (Equation 8), the excitation current target values may be a periodic function obtained by adding an offset value to a trigonometric function having the scan angle $\theta$ as an angle variable. Furthermore, the excitation current target value for each winding may be a general periodic function having the scan angle $\theta$ as an angle variable, which is defined so that the flatness of the magnetic flux density in the internal space of the scanning magnet 1 is improved and the change in the flatness with respect to the change in the scan angle $\theta$ is suppressed.

The scanning magnet 1 may include a plurality N (four or more) of windings. Each of the plurality N of windings has the forward section and the backward section extending along the trajectory of the charged particle beam, and the plurality N of windings surround the columnar space through which the charged particle beam passes. The forward section and the backward section in each winding are arranged at a predetermined interval when viewed in the outer circumferential direction of the columnar space. The forward section or the backward section of one winding among the plurality of windings are disposed between the forward section and the backward section of another winding.

The magnetic flux density for deflecting the charged particle beam in a direction represented by the scan angle $\theta$ and the kick angle $\psi$ (I) is generated in the columnar space in a manner that a current flowing through the plurality N of windings approaches or coincides with the excitation current target value represented by the following (Equation 9) in a state where the plurality of windings have such a distributed winding structure. As the distributed winding structure of the plurality of windings, a distributed winding structure of stator windings of an AC motor or an AC generator may be applied.

When the N windings $C_0$ to $C_{N-1}$ are provided, the command conversion device 20 obtains the excitation current target values $I_1^*$ to $I_{N-1}^*$ for the windings $C_0$ to $C_{N-1}$ by designating the kick angle $\psi$ and the scan angle $\theta$, and outputs the excitation current target values to the scanning magnet control apparatus 22. The DC current target value $I_k^*$ (k is an integer of 0 to N-1) is a value obtained according to (Equation 9).

$$I_k^* = I \cdot \sin(\theta - k \cdot 2\pi/N) \quad \text{(Equation 9)}$$

The scanning magnet control apparatus 22 controls drive circuits of the windings $C_0$ to $C_{N-1}$ so that the excitation current flowing through the winding $C_k$ approaches or coincides with the excitation current target value $I_k^*$. Thus, the charged particle beam is directed in a direction determined by the kick angle $\psi$ and the scan angle $\theta$. Also for (Equation 9), the offset value $\Delta I_k$ for each winding $C_k$ may be added. The offset value $\Delta I_k$ may be a function having the scan angle θ as a variable.

The excitation current target value for each winding may be a general periodic function having the scan angle θ as an angle variable, which is defined so that the flatness of the magnetic flux density in the internal space of the scanning magnet 1 is improved and the change in the flatness with respect to the change in the scan angle θ is suppressed.

When the outer circumferential direction of the columnar space is taken on a horizontal axis and the magnetomotive force is taken on a vertical axis, the distribution of the magnetomotive force in the circumferential direction becomes distribution approximate to a sine wave by the same principle as in the case of including three windings. Thus, the flatness of the magnetic flux density when viewed in the direction crossing magnetic force lines. In addition, since the distribution of the magnetomotive force in the circumferential direction for all scan angles θ is distribution approximate to a sine wave, the change in the flatness with respect to the change in the scan angle θ is suppressed, and variations in the kick angle and the kick amount of the charged particle beam due to the difference in the scan angle θ are suppressed.

Figure 9:
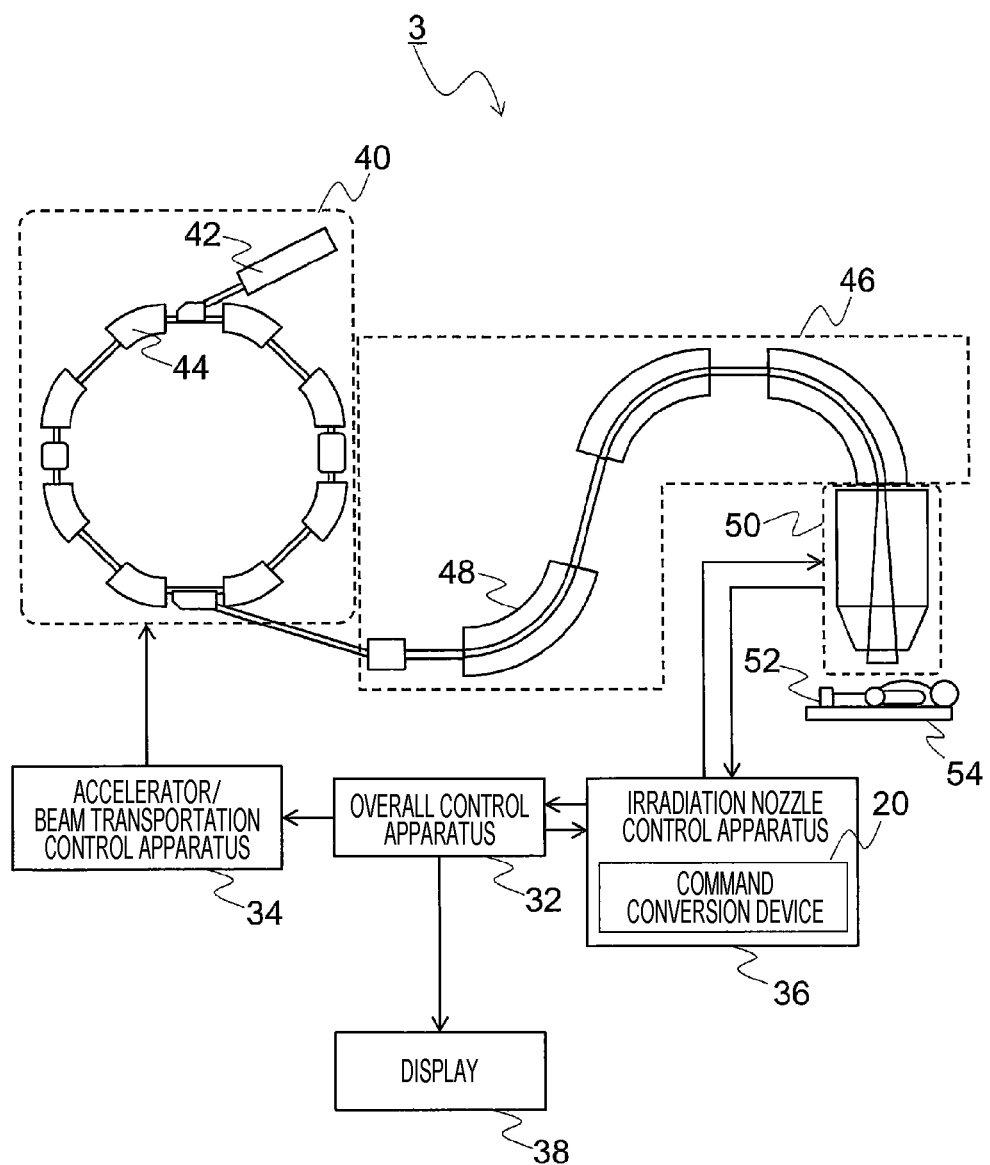
FIG. 9 is a diagram illustrating an overall configuration of a particle therapy system.

Next, a particle therapy system using the scanning magnet 1 will be described. FIG. 9 illustrates an overall configuration of a particle therapy system 3. The particle therapy system 3 is a system that irradiates a target volume of a patient 52 with radiation from an irradiation nozzle 50. The particle therapy system 3 includes an accelerator 40 that accelerates a charged particle beam, a beam transport device 46 that transports the accelerated charged particle beam to the irradiation nozzle 50, the irradiation nozzle 50 that irradiates a target volume with the charged particle beam, and a couch 54.

The particle therapy system 3 further includes an overall control apparatus 32, an accelerator/beam transportation control apparatus 34, an irradiation nozzle control apparatus 36, and a display 38. The irradiation nozzle control apparatus 36 includes the command conversion device 20 described above.

The overall control apparatus 32, the accelerator/beam transportation control apparatus 34, and the irradiation nozzle control apparatus 36 may include a processor. The processors constituting the overall control apparatus 32, the accelerator/beam transportation control apparatus 34, and the irradiation nozzle control apparatus 36 execute a program stored in a memory in the particle therapy system 3 or a program read from the outside, to perform processing of controlling the device as a control target.

The accelerator 40 includes an injector 42 and a synchrotron accelerator 44. A charged particle beam that is accelerated to about 60% to 70% of a light speed by the accelerator 40 and is extracted is transported to the irradiation nozzle 50 while being deflected in vacuum by a bending magnet 48 disposed in the beam transport device 46. A charged particle beam 90 is shaped by the irradiation nozzle 50 so as to match the shape of the irradiation region, and is irradiated to the irradiation target. The irradiation target is, for example, a target volume of the patient 52 laid on the couch 54.

Figure 10:
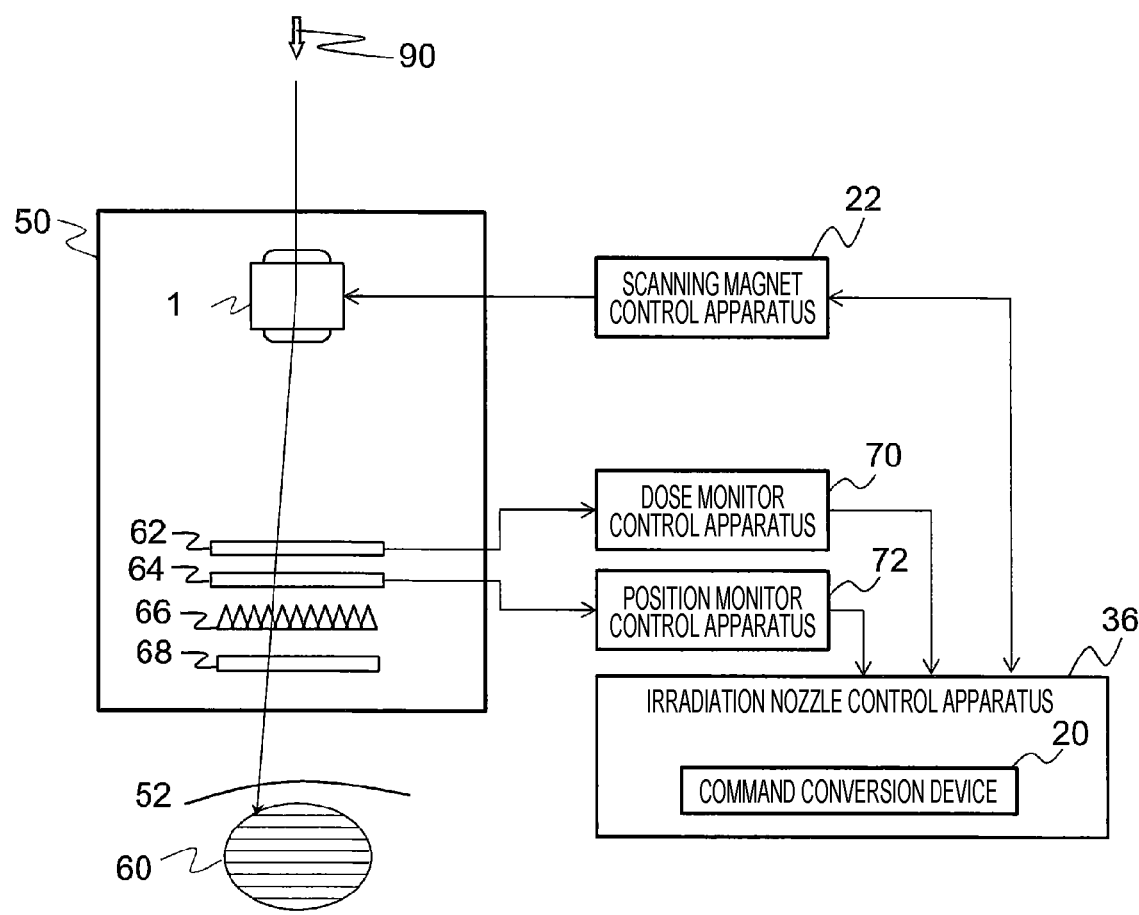
FIG. 10 is a diagram illustrating a configuration of an irradiation nozzle for particle beam scanning.
Figure 11:
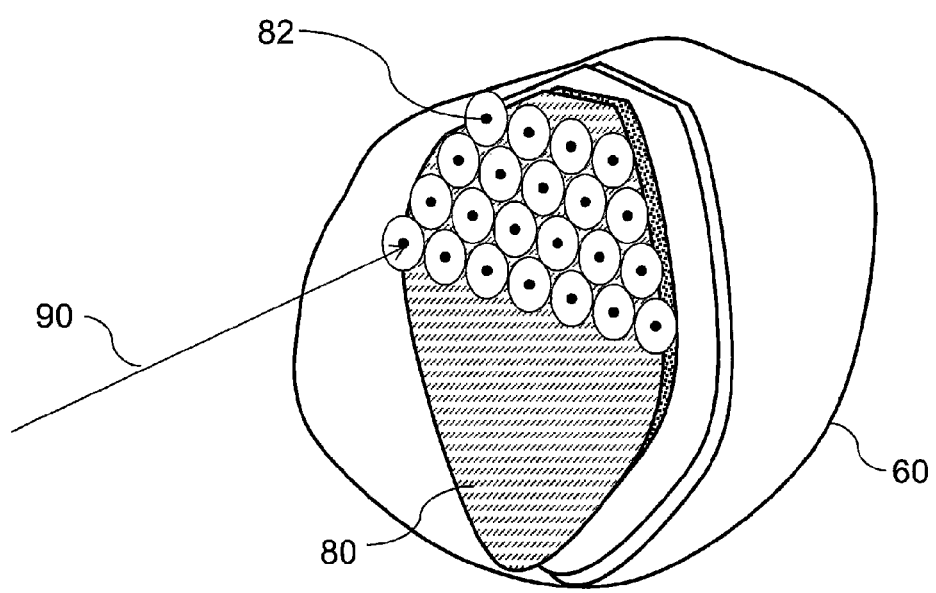
FIG. 11 is a diagram illustrating an irradiation spot in a target volume.
Figure 12:
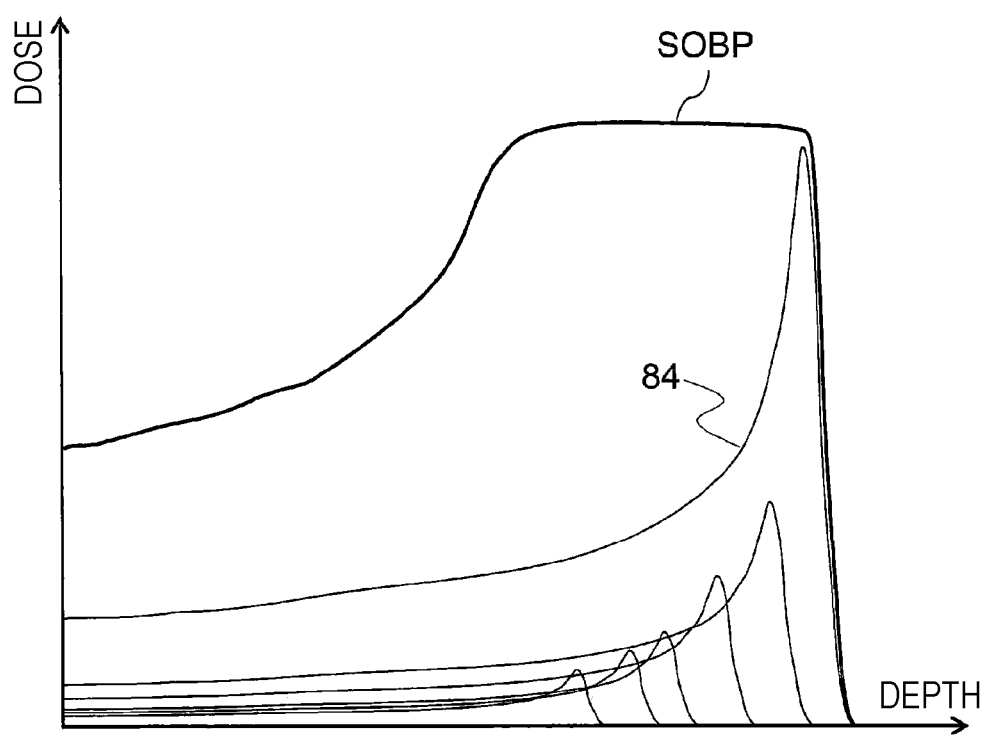
FIG. 12 is a diagram illustrating dose distribution in a depth direction in scanning irradiation.

Next, details of the irradiation nozzle 50 and the peripheral device will be described with reference to FIGS. 10 to 12. FIG. 10 illustrates a configuration of the irradiation nozzle 50 for particle beam scanning. FIG. 11 illustrates the charged particle beam 90 when the target volume 60 is scanned and irradiated, a layer 80 irradiated with the same energy, and an irradiation spot 82. FIG. 12 illustrates the dose distribution in the depth direction when the target volume 60 is scanned and irradiated.

In the irradiation nozzle 50, the charged particle beam 90 is scanned in a two-dimensional plane perpendicular to the passing direction of the charged particle beam 90. The target volume 60 is irradiated with the charged particle beam 90 scanned by the scanning magnet 1.

A dose monitor 62 is a monitor for collecting electrons generated by the passage of the charged particle beam 90 in order to calculate the dose of the charged particle beam 90 with which each irradiation spot 82 is irradiated. A detection signal (pulse signal obtained by collecting electrons) of the dose monitor 62 is output to a dose monitor control apparatus 70.

The dose monitor control apparatus 70 and a position monitor control apparatus 72 may include a processor. The processors constituting the dose monitor control apparatus 70 and the position monitor control apparatus 72 execute a program stored in the memory in the particle therapy system 3 or a program read from the outside, to perform processing of controlling the device as each control target.

The dose monitor control apparatus 70 calculates the irradiation amount with which each irradiation spot 82 is irradiated based on the detection signal output from the dose monitor 62, and outputs the calculated irradiation amount to the irradiation nozzle control apparatus 36.

A position monitor 64 is a monitor for collecting electrons generated by the passage of the charged particle beam 90 in order to calculate the position (for example, the position of the center of gravity) of each irradiation spot 82. A detection signal (pulse signal obtained by collecting electrons) of the position monitor 64 is output to the position monitor control apparatus 72.

The position monitor control apparatus 72 counts the dose in each irradiation spot 82 based on the detection signal output from the position monitor 64, and outputs the calculated count value to the irradiation nozzle control apparatus 36.

The irradiation nozzle control apparatus 36 obtains the passing position of the charged particle beam 90 based on the signal output from the position monitor control apparatus 72, calculates the position and the width of the irradiation spot 82 from data of the obtained passing position, and confirms the irradiation position of the charged particle beam 90. The irradiation nozzle control apparatus 36 controls the irradiation of the charged particle beam 90 in accordance with the detection signal output from the dose monitor control apparatus 70.

A ridge filter 66 is used when it is necessary to thicken the Bragg peak. A range shifter 68 may be inserted when the arrival position of the charged particle beam 90 is adjusted.

In the scanning irradiation, the position of each irradiation spot 82 and the target irradiation amount for each irradiation spot 82 for irradiating the target volume 60 with uniform dose distribution by a therapy planning device (not illustrated) are calculated in advance.

As illustrated in FIG. 11, in the scanning irradiation, the target volume 60 is divided into a plurality of layers 80, and one or more irradiation spots 82 are disposed in one layer 80. In each layer 80, the irradiation spots 82 are sequentially irradiated with the charged particle beam 90 having the same energy.

When the energy of the charged particle beam 90 changes, the arrival position of the charged particle beam 90 changes. That is, the charged particle beam 90 reaches a deeper position in the body as the energy is higher. Therefore, in order to change the traveling direction of the charged particle beam 90, that is, the irradiation position in the depth direction of the target volume 60, the energy of charged particle beam 90 is changed.

In the scanning irradiation, irradiation indicated by SOBP (Spread Out Bragg Peak) is performed. The SOBP means distribution in which the dose in the depth direction is made uniform by appropriately distributing the irradiation dose to a plurality of charged particle beams having different energies. FIG. 12 illustrates the SOBP as the dose distribution in the depth direction of the target volume. Irradiation indicated by each Bragg curve 84 is performed for each energy by appropriately distributing the irradiation dose to each of a plurality of charged particle beams having different energies, and the dose distribution in the depth direction of the target volume becomes the SOBP. That is, the Bragg curves 84 corresponding to the respective energies are superimposed, and irradiation indicated by uniform dose distribution in the depth direction is performed as illustrated in FIG. 12.

Figure 13:
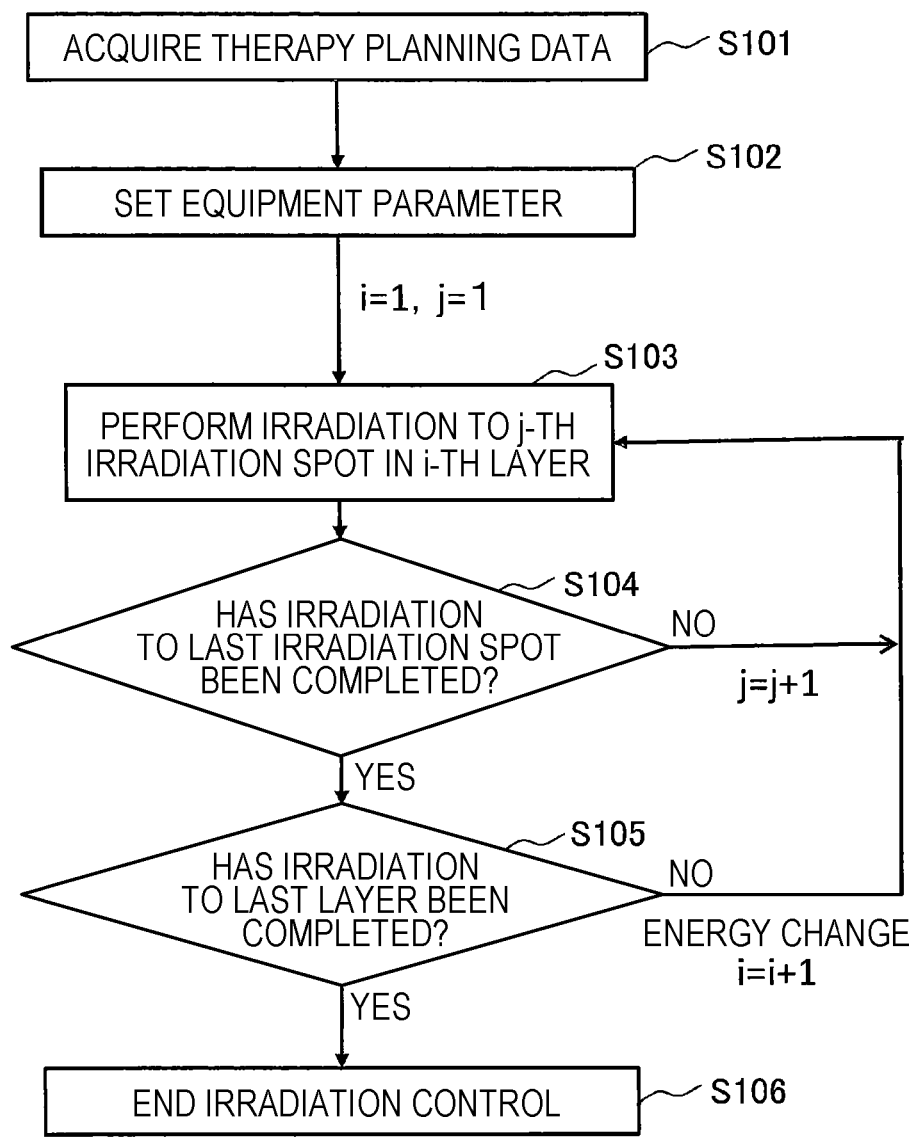
FIG. 13 is a flowchart during irradiation.

FIG. 13 illustrates the flowchart during irradiation. Therapy plan data for each patient, which is created in advance by the therapy planning device is transmitted from the therapy planning device to an OIS (Oncology Information System) and stored in the OIS. The therapy plan data is transmitted from the OIS to the overall control apparatus 32 in the particle therapy system 3 illustrated in FIG. 9. The overall control apparatus 32 may display information indicating an operation state or the like of the particle therapy system 3 on the display 38. In Step S101, the overall control apparatus 32 acquires the therapy plan data transmitted from the OIS.

In Step S102, the overall control apparatus 32 sets equipment parameters for controlling the couch 54, the accelerator/beam transportation control apparatus 34, and the irradiation nozzle control apparatus 36 based on the therapy plan data. The overall control apparatus 32 controls the couch 54, the accelerator/beam transportation control apparatus 34, and the irradiation nozzle control apparatus 36 based on the equipment parameters.

For example, the overall control apparatus 32 transmits data representing the energy of each irradiation spot, the coordinate values (X, Y) of the irradiation position, the irradiation amount, and the like, to the irradiation nozzle control apparatus 36 as the equipment parameters. The command conversion device 20 in the irradiation nozzle control apparatus 36 converts the coordinate values (X, Y) of the irradiation position into the excitation current target values Iu*, Iv*, and Iw*, and transmits the excitation current target values to the scanning magnet control apparatus 22.

In Step S103, the accelerator/beam transportation control apparatus 34 and the irradiation nozzle control apparatus 36 control the accelerator 40, the beam transport device 46, and the irradiation nozzle 50 under the control of the overall control apparatus 32. Thus, the j-th irradiation spot in the i-th layer is irradiated with the charged particle beam 90 (S103).

Here, i is an integer of 1 to K, and is used for specifying the layer set in the target volume 60. j is an integer of 1 to M(K), and is used for specifying the irradiation spot in the i-th layer. In the first irradiation, i=1 and j=1. The integer M(K) is used for specifying the last irradiation spot in the last layer. For each irradiation spot with the charged particle beam, the couch 54 sets the position and posture of the patient 52 to an appropriate position under the control of the overall control apparatus 32.

In Step S104, the overall control apparatus 32 determines whether the irradiation of the last irradiation spot in the layer of the target volume 60 has been completed. When it is determined that the irradiation is not completed, the overall control apparatus 32 returns to the control of Step S103 by increasing j by 1. When the overall control apparatus 32 determines that the irradiation of the last irradiation spot in the layer of the target volume 60 has been completed in Step S104, the overall control apparatus 32 determines whether the irradiation of the last layer has been completed, in Step S105. When it is determined that the irradiation of the last layer is not completed, the overall control apparatus 32 increases i by 1 to change the energy, and returns to Step S103 to irradiate the next layer. When the overall control apparatus 32 determines that the irradiation of the last layer has been completed, the overall control apparatus 32 ends the irradiation control (S106).

Figure 14:
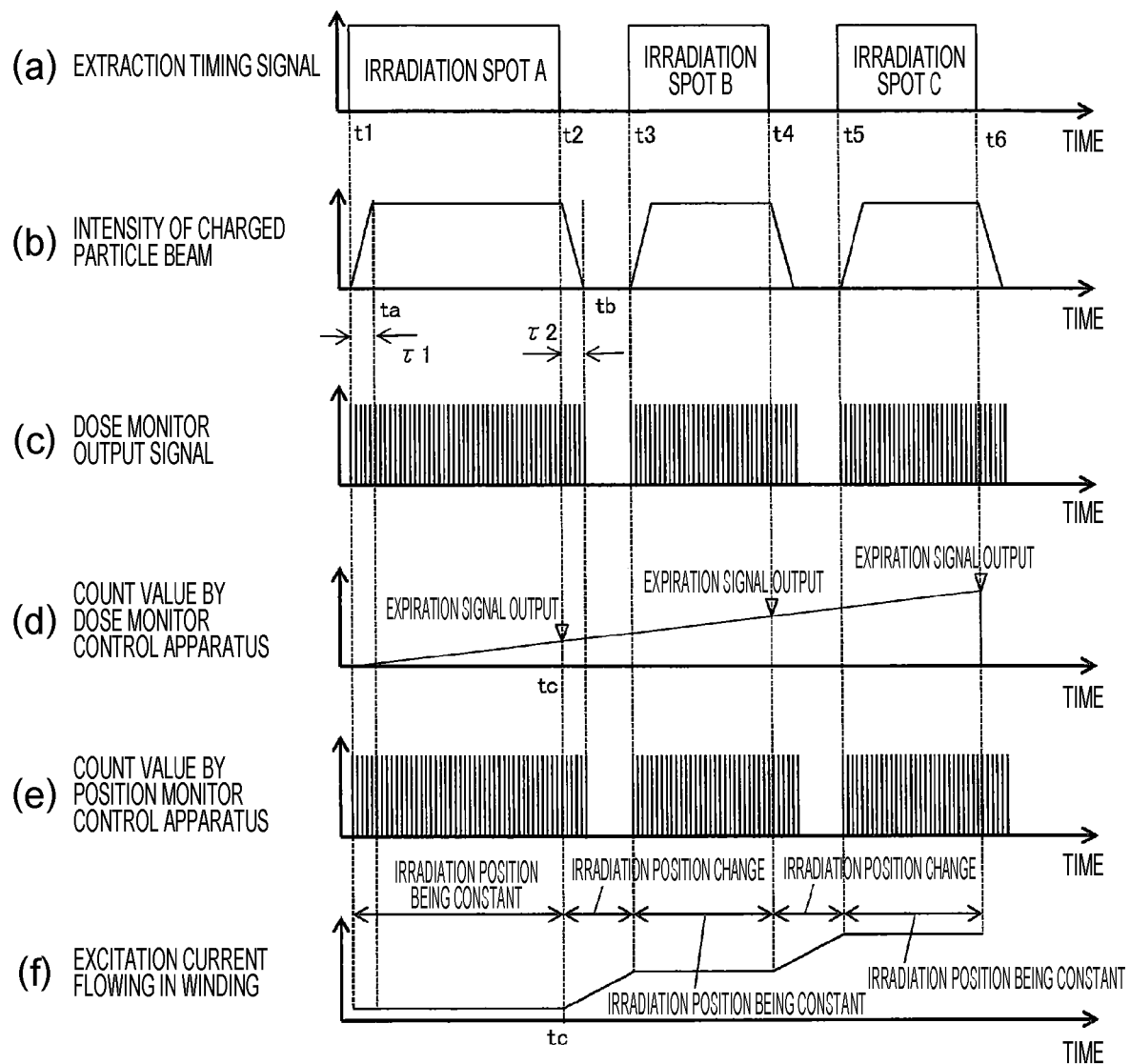
FIG. 14 is a timing chart of scanning irradiation.

FIGS. 14(*a*) to 14(*f*) conceptually illustrate timing charts of the scanning irradiation. Here, an example in which three irradiation spots from an irradiation spot A to an irradiation spot C are irradiated with the charged particle beam is illustrated. As illustrated in FIG. 14(*a*), in the irradiation of the irradiation spot A, an extraction timing signal is output from the accelerator/beam transportation control apparatus 34 to the accelerator 40 at times t1 to t2, and a command to require extraction of the charged particle beam is issued to the accelerator 40.

The extraction timing signal is output from the accelerator/beam transportation control apparatus 34 to the accelerator 40 at times t3 to t4 in the irradiation of the irradiation spot B and at times t5 to t6 in the irradiation of the irradiation spot C, and a command to require extraction of the charged particle beam is issued to the accelerator 40. The accelerator/beam transportation control apparatus 34 outputs a command to the accelerator 40 so that the target volume is irradiated with the charged particle beam 90 having predetermined intensity in this manner.

Since irradiation of each of the irradiation spots of the irradiation spot A to the irradiation spots C is performed by similar processing, the irradiation of the irradiation spot A will be described here. As illustrated in FIG. 14(*b*), after the extraction timing signal rises at the time t1, the intensity of the charged particle beam increases. The intensity of the charged particle beam reaches the maximum value at time to after a lapse of time $\tau 1$ from the time t1. After the extraction timing signal falls at the time t2, the intensity of the charged particle beam decreases. The intensity of the charged particle beam becomes 0 at time tb after a lapse of time $\tau 2$ from the time t2.

As illustrated in FIG. 14(*c*), when the irradiation with the charged particle beam 90 is started at the time t1, the dose monitor 62 in the irradiation nozzle 50 converts an ionization output into a pulse signal as the detection signal and outputs the pulse signal to the dose monitor control apparatus 70. As illustrated in FIG. 14(*d*), when a pulse count value counted by the dose monitor control apparatus 70 increases with the irradiation with the charged particle beam and the pulse count value reaches a predetermined value at time tc, the dose monitor control apparatus 70 transmits an expiration signal to the irradiation nozzle control apparatus 36. Thus, the irradiation nozzle control apparatus 36 stops the irradiation of the irradiation spot with the charged particle beam.

As illustrated in FIG. 14(*e*), while the irradiation spot A is irradiated with the charged particle beam, similarly to the dose monitor 62, the position monitor 64 also converts the ionization output into a pulse signal as the detection signal and outputs the pulse signal to the position monitor control apparatus 72. When the irradiation of the irradiation spot A is ended, the position monitor control apparatus 72 outputs the pulse count value for one irradiation spot to the irradiation nozzle control apparatus 36. The irradiation nozzle control apparatus 36 calculates the position and the width of the irradiation spot based on the count value output from the position monitor control apparatus 72, and determines whether or not the charged particle beam 90 is irradiated to a predetermined position. As a result of the determination, when the shift of the spot position or the width exceeds a predetermined value, the irradiation of the irradiation spot with the charged particle beam is stopped.

By the expiration signal output from the dose monitor control apparatus 70, the command conversion device 20 in the irradiation nozzle control apparatus 36 obtains the excitation current target values Iu*, Iv*, and Iw* corresponding to the next irradiation position, and transmits the excitation current target values Iu*, Iv*, and Iw* to the scanning magnet control apparatus 22. The scanning magnet control apparatus 22 controls the excitation currents flowing through the winding U, the winding V, and the winding W by using the excitation current target values Iu*, Iv*, and Iw*.

FIG. 14(f) illustrates changes in the excitation current flowing through the winding U, the winding V, and the winding W. The excitation current is constant during a period from the time t1 when the extraction timing signal rises to the time tc when the extraction timing signal starts to fall. In this time zone, the xy coordinate values (X, Y) of the irradiation position is constant. During a period from the time tc to the time t3 when the extraction timing signal rises for the irradiation of the next irradiation spot B, the value of the excitation current approaches the next excitation current target value and reaches the excitation current target value. The xy coordinate values (X, Y) of the irradiation position changes in this time zone.

Here, the irradiation of the irradiation spot A with the charged particle beam has been described, but the irradiation of the irradiation spot B and the irradiation spot C with the charged particle beam is also performed by similar processing.

Next, effects of the scanning magnet 1 according to the present embodiment will be described. Since the scanning magnet 1 two-dimensionally scans the charged particle beam 90, the irradiation nozzle 50 is smaller than when two scanning magnets for scanning the charged particle beam in one direction are used. In addition, by arranging the scanning magnet 1 on the further upstream side, the scanning of the charged particle beam becomes faster than the case using two scanning magnets for scanning the charged particle beam in one direction, and the radiation field is enlarged. Furthermore, since the size of the scanning magnet 1 for obtaining a predetermined kick amount is reduced, the excitation current flowing through each winding decreases. Thus, the drive circuit that controls the current flowing through each winding becomes small.

Figures 15, 16, 17:
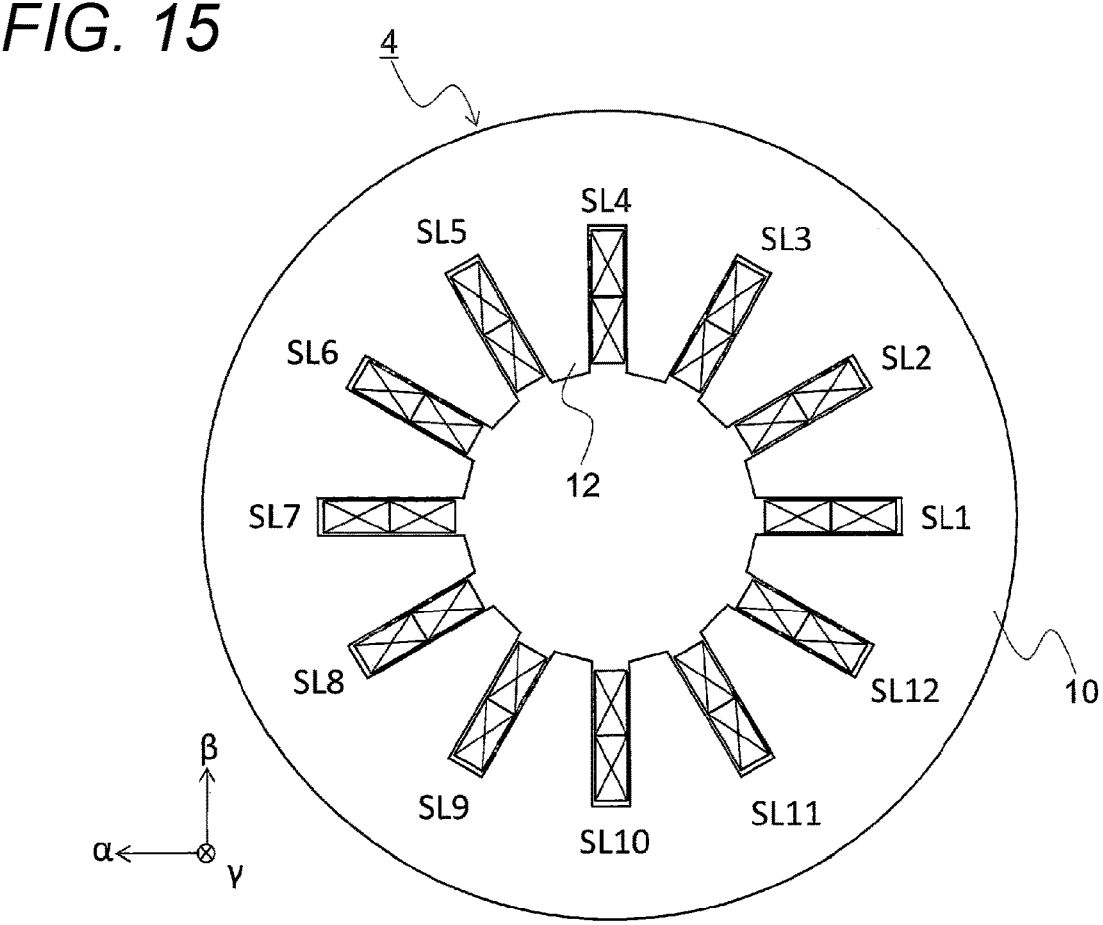
FIG. 15 is a diagram schematically illustrating a cross-sectional shape of the scanning magnet.
FIG. 16 is a diagram illustrating a correspondence relation between a groove and a winding section disposed in the groove.
FIG. 17 is a diagram illustrating a correspondence relation between the groove and the winding section disposed in the groove.

A scanning magnet 4 according to a second embodiment of the present invention will be described with reference to FIGS. 15 to 17. FIG. 15 schematically illustrates a cross-sectional shape of the scanning magnet 4 when viewed from the upstream side of the trajectory of the charged particle beam. In FIG. 16, which one of the winding sections U+, U−, V+, V−, W+, and W− is disposed in each of the grooves SL1 to SL12 is illustrated for each of the outer side and the inner side of each groove by the similar notation to in FIG. 3.

Twelve grooves SL1 to SL12 are formed on the inner wall surface of a yoke 10 counterclockwise at 30° intervals in this order. The grooves SL1 to SL12 are recessed outward and extend in the axial direction. A tooth 12 is formed between the adjacent grooves. Each tooth 12 has a shape protruding to the inside of the yoke 10 with reference to the deepest portions of the grooves SL1 to SL12.

A winding U is provided on the outer side and the inner side of each of the grooves SL1 and SL2, and the outer side and the inner side of the grooves SL7 and SL8 facing the grooves SL1 and SL2. When a passing direction of a conductive wire forming the winding U is defined such that the conductive wire passes through the grooves SL1 and SL2 in the γ-axis positive direction, the conductive wire forming the winding U passes through the grooves SL7 and SL8 in the γ-axis negative direction.

More specifically, the conductive wire forming the winding U winds around a loop path SL1 (in)-SL7 (out) in which the inner side of the groove SL1 is directed to the γ-axis positive direction, and the outer side of the groove SL7 is directed to the γ-axis negative direction. The conductive wire forming the winding U winds around a loop path SL1 (out)-SL7 (in) in which the outer side of the groove SL1 is directed to the γ-axis positive direction, and the inner side of the groove SL7 is directed to the γ-axis negative direction. Further, the conductive wire forming the winding U winds around a loop path SL2 (in)-SL8 (out) in which the inner side of the groove SL2 is directed to the γ-axis positive direction, and the outer side of the groove SL8 is directed to the γ-axis negative direction. The conductive wire forming the winding U winds around a loop path SL2 (out)-SL8 (in) in which the outer side of the groove SL2 is directed to the γ-axis positive direction, and the inner side of the groove SL8 is directed to the γ-axis negative direction. When a current flows in the γ-axis positive direction in the winding section U+ disposed in the grooves SL1 and SL2, a current flows in the γ-axis negative direction in the winding section U− disposed in the grooves SL7 and SL8.

The conductive wire forming the winding U may be arranged in any manner, under a current polarity condition that the current flows in the winding section U− as the backward section in the γ-axis negative direction when the current flows in the winding section U+ as the forward section in the γ-axis positive direction. That is, under such a current polarity condition, the conductive wire forming the winding U may pass through the inner side and the outer side of each of the grooves SL1, SL2, SL7, and SL8 in any order.

A winding V is provided on the outer side and the inner side of each of the grooves SL5 and SL6, and the outer side and the inner side of the grooves SL11 and SL12 facing the grooves SL5 and SL6. When the passing direction of a conductive wire forming the winding V is defined such that the conductive wire passes through the grooves SL5 and SL6 in the γ-axis positive direction, the conductive wire forming the winding V passes through the grooves SL11 and SL12 in the γ-axis negative direction.

More specifically, the conductive wire forming the winding V winds around a loop path SL5 (in)-SL11 (out) in which the inner side of the groove SL5 is directed to the γ-axis positive direction, and the outer side of the groove SL11 is directed to the γ-axis negative direction. The conductive wire forming the winding V winds around a loop path SL5 (out)-SL11 (in) in which the outer side of the groove SL5 is directed to the γ-axis positive direction, and the inner side of the groove SL11 is directed to the γ-axis negative direction. Further, the conductive wire forming the winding V winds around a loop path SL6 (in)-SL12 (out) in which the inner side of the groove SL6 is directed to the γ-axis positive direction, and the outer side of the groove SL12 is directed to the γ-axis negative direction. The conductive wire forming the winding V winds around a loop path SL6 (out)-SL12

(in) in which the outer side of the groove SL6 is directed to the γ-axis positive direction, and the inner side of the groove SL12 is directed to the γ-axis negative direction. When a current flows in the γ-axis positive direction in the winding section V+ disposed in the grooves SL5 and SL6, a current flows in the γ-axis negative direction in the winding section V− disposed in the grooves SL11 and SL12.

The conductive wire forming the winding V may be arranged in any manner, under a current polarity condition that the current flows in the winding section V− as the backward section in the γ-axis negative direction when the current flows in the winding section V+ as the forward section in the γ-axis positive direction. That is, under such a current polarity condition, the conductive wire forming the winding V may pass through the inner side and the outer side of each of the grooves SL5, SL6, SL11, and SL12 in any order.

A winding W is provided on the outer side and the inner side of each of the grooves SL3 and SL4, and the outer side and the inner side of the grooves SL9 and SL10 facing the grooves SL3 and SL4. When the passing direction of a conductive wire forming the winding W is defined such that the conductive wire passes through the grooves SL9 and SL10 in the γ-axis positive direction, the conductive wire forming the winding W passes through the grooves SL3 and SL4 in the γ-axis negative direction.

More specifically, the conductive wire forming the winding W winds around a loop path SL10 (in)-SL4 (out) in which the inner side of the groove SL10 is directed to the γ-axis positive direction, and the outer side of the groove SL4 is directed to the γ-axis negative direction. The conductive wire forming the winding W winds around a loop path SL10 (out)-SL4 (in) in which the outer side of the groove SL10 is directed to the γ-axis positive direction, and the inner side of the groove SL4 is directed to the γ-axis negative direction. Further, the conductive wire forming the winding W winds around a loop path SL9 (in)-SL3 (out) in which the inner side of the groove SL9 is directed to the γ-axis positive direction, and the outer side of the groove SL3 is directed to the γ-axis negative direction. The conductive wire forming the winding W winds around a loop path SL9 (out)-SL3 (in) in which the outer side of the groove SL9 is directed to the γ-axis positive direction, and the inner side of the groove SL3 is directed to the γ-axis negative direction. When a current flows in the γ-axis positive direction in the winding section W+ disposed in the grooves SL9 and SL10, a current flows in the γ-axis negative direction in the winding section W− disposed in the grooves SL3 and SL4.

The conductive wire forming the winding W may be arranged in any manner, under a current polarity condition that the current flows in the winding section W− as the backward section in the γ-axis negative direction when the current flows in the winding section W+ as the forward section in the γ-axis positive direction. That is, under such a current polarity condition, the conductive wire forming the winding W may pass through the inner side and the outer side of each of the grooves SL3, SL4, SL9, and SL10 in any order.

As described above, the yoke 10, the winding U, the winding V, and the winding W have a 120° rotationally symmetric structure with respect to the central axis of the yoke 10. That is, the winding U, the winding V, and the winding W have a 120° rotationally symmetric structure around an axis of the columnar space surrounded by the yoke 10.

In the winding structure illustrated in FIG. 16, a plurality of forward sections in each winding are arranged adjacent to each other as a forward section group, and a plurality of backward sections in each winding are arranged adjacent to each other as a backward section group. The forward section group or the backward section group of one windings among the winding U, the winding V, and the winding W is disposed between the forward section group and the backward section group of another winding.

Specifically, in the winding structure illustrated in FIG. 16, the forward section group of the winding U includes four forward sections U+ disposed on the outer side and the inner side of each of the grooves SL1 and SL2. The backward section group of the winding U includes four backward sections U− disposed on the outer side and the inner side of each of the grooves SL7 and SL8.

Each of the forward section group and the backward section group of the winding V has a structure obtained by rotating the forward section group and the backward section group of the winding U counterclockwise by 120° around the center axis of the yoke 10. Each of the forward section group and the backward section group of the winding W has a structure obtained by rotating the forward section group and the backward section group of the winding V counterclockwise by 120° around the center axis of the yoke 10.

The scanning magnet 4 according to the second embodiment has a larger number of loop paths of windings than the scanning magnet 1 according to the first embodiment. Thus, the distribution of the magnetomotive force in the outer circumferential direction of the columnar space is distribution approximated by a sine wave. Thus, effects that the flatness of the magnetic flux density is improved, the change in the flatness with respect to the change in the scan angle θ is suppressed, and the variation in the kick angle of the charged particle beam due to the difference in the scan angle θ is suppressed are enhanced.

FIG. 17 illustrates another arrangement example of the winding sections U+, U−, V+, V−, W+, and W− in the grooves SL1 to SL12 by the similar notation to FIG. 3. The conductive wire forming the winding U winds around a loop path SL1 (in)-SL6 (out) in which the inner side of the groove SL1 is directed to the γ-axis positive direction, and the outer side of the groove SL6 is directed to the γ-axis negative direction. The conductive wire forming the winding U winds around a loop path SL2 (in)-SL7 (out) in which the inner side of the groove SL2 is directed to the γ-axis positive direction, and the outer side of the groove SL7 is directed to the γ-axis negative direction. The conductive wire forming the winding U winds around a loop path SL1 (out)-SL8 (in) in which the outer side of the groove SL1 is directed to the γ-axis positive direction, and the inner side of the groove SL8 is directed to the γ-axis negative direction. Further, the conductive wire forming the winding U winds around a loop path SL12 (out)-SL7 (in) in which the outer side of the groove SL12 is directed to the γ-axis positive direction, and the inner side of the groove SL7 is directed to the γ-axis negative direction.

The winding V has a structure similar to a structure obtained by rotating the winding U counterclockwise by 120° around the center axis of the yoke 10 in FIG. 15. The winding W has a structure similar to a structure obtained by rotating the winding V counterclockwise by 120° around the center axis of the yoke 10 in FIG. 15. As described above, the yoke 10, the winding U, the winding V, and the winding W have a 120° rotationally symmetric structure around an axis of the columnar space surrounded by the yoke 10.

Also in the winding structure illustrated in FIG. 17, similar to FIG. 16, a plurality of forward sections in each winding are arranged adjacent to each other as a forward section group, and a plurality of backward sections in each winding are arranged adjacent to each other as a backward section group. The forward section group or the backward section group of one windings among the winding U, the winding V, and the winding W is disposed between the forward section group and the backward section group of another winding.

Specifically, in the winding structure illustrated in FIG. 17, the forward section group of the winding U includes four forward sections U+ disposed on the outer side of the groove SL12, the inner side and the outer side of the groove SL1, and the inner side of the groove SL2. The backward section group of the winding U includes four backward sections U− disposed on the outer side of the groove SL6, the inner side and the outer side of the groove SL7, and the inner side of the groove SL8.

Each of the forward section group and the backward section group of the winding V has a structure obtained by rotating the forward section group and the backward section group of the winding U counterclockwise by 120° around the center axis of the yoke 10. Each of the forward section group and the backward section group of the winding W has a structure obtained by rotating the forward section group and the backward section group of the winding V counterclockwise by 120° around the center axis of the yoke 10.

The conductive wire forming the winding U may be arranged in any manner, under a current polarity condition that the current flows in the winding section U− as the backward section in the γ-axis negative direction when the current flows in the winding section U+ as the forward section in the γ-axis positive direction. Similarly, for the winding sections V+ and V− of the winding V and the winding sections W+ and W− of the winding W, the conductive wire forming each winding may be disposed in any manner.

In the scanning magnet in which the windings are arranged as illustrated in FIG. 17, in comparison to the scanning magnet in which the windings are arranged as illustrated in FIG. 16, the distribution of the magnetomotive force in the circumferential direction is distribution more approximate to a sine wave. Thus, effects that the flatness of the magnetic flux density is improved, the change in the flatness with respect to the change in the scan angle θ is suppressed, and the variation in the kick angle of the charged particle beam due to the difference in the scan angle θ is suppressed are enhanced.

Figure 18:
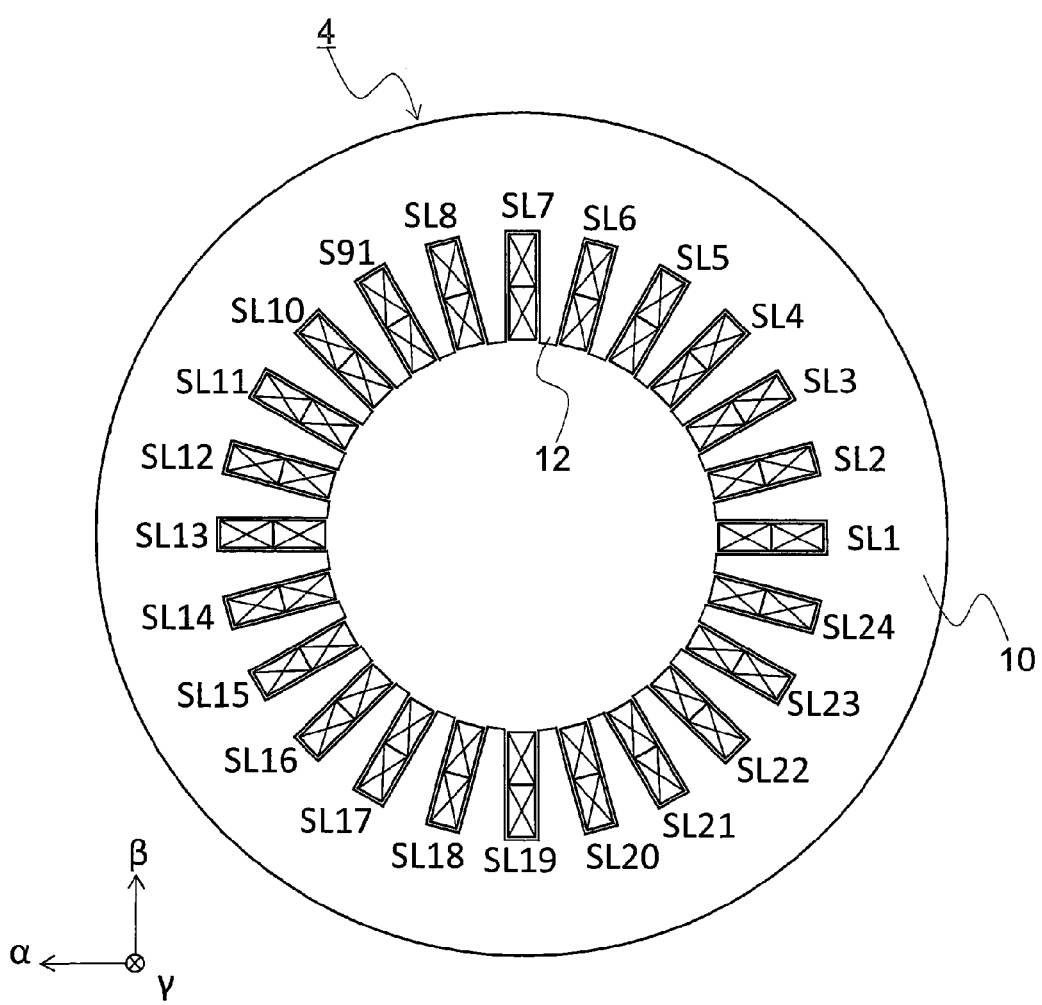
FIG. 18 is a diagram schematically illustrating a cross-sectional shape of a scanning magnet.

In the scanning magnet, the number of grooves in the inner wall of the yoke 10 may be further increased. However, the number of grooves is set to a multiple of 6. As an example, FIG. 18 illustrates a cross-sectional view of the scanning magnet 4 configured by 24 grooves SL1 to SL24. By increasing the loop path formed by the grooves, the distribution of the magnetomotive force in the circumferential direction of the columnar space becomes more approximate to a sinusoidal waveform. Thus, effects that the flatness of the magnetic flux density is improved, the change in the flatness with respect to the change in the scan angle θ is suppressed, and the variation in the kick angle of the charged particle beam due to the difference in the scan angle θ is suppressed are enhanced.

When one winding winds around a plurality of loop paths, a section winding around one loop path in one winding and a section winding around another loop path may be connected in series or in parallel. For example, for the winding U illustrated in FIG. 16, a section passing through the loop path SL1(in) to SL7(out), a section passing through the loop path SL1(out) to SL7(in), a section passing through the loop path SL2(in) to SL8(out), and a section passing through the loop path SL2(out) to SL8(in) may be connected in series or in parallel. The above description is similarly applied to the winding V and the winding W.

For the winding U illustrated in FIG. 17, a section passing through the loop path SL1(in) to SL6(out), a section passing through the loop path SL2(in) to SL7(out), a section passing through the loop path SL1(out) to SL8(in), and a section passing through the loop path SL12(out) to SL7(in) may be connected in series or in parallel. The above description is similarly applied to the winding V and the winding W.

Figure 19:
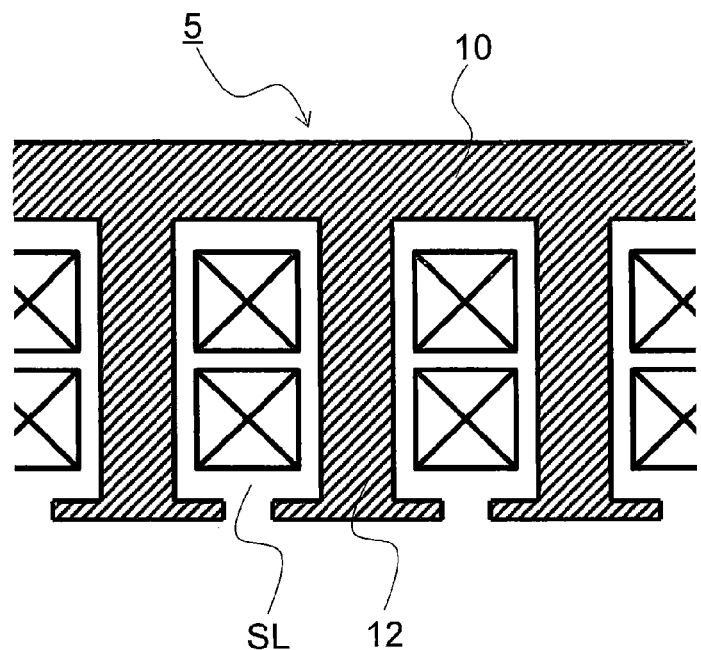
FIG. 19 is an enlarged view of a tooth portion.

FIG. 19 illustrates a scanning magnet 5 according to a third embodiment of the present invention. In FIG. 19, in a cross section of the scanning magnet 5 viewed from the upstream side of the trajectory of the charged particle beam, a portion of a tooth 12 is illustrated in an enlarged manner. As illustrated in FIG. 19, the distal end portion of the tooth 12 formed between the adjacent grooves is widened in the circumferential direction of the inner wall of a yoke 10. The flatness of the magnetic flux density may be improved by forming the distal end portion of the tooth 12 in a shape widening in the circumferential direction.

Figure 20:
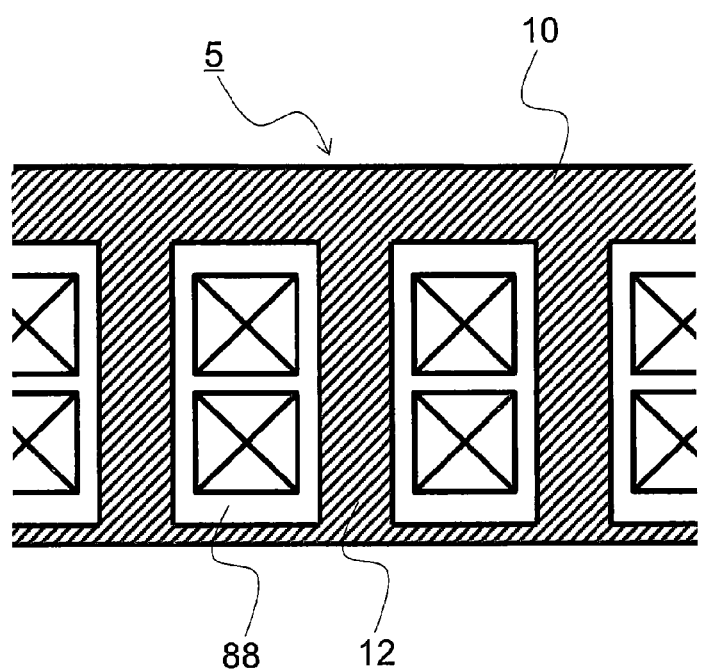
FIG. 20 is a diagram illustrating a structure in which a hole extending in an axial direction is provided instead of the groove.

As illustrated in FIG. 20, the similar effect may be obtained by adopting a shape of eliminating a space between the adjacent teeth 12, that is, a structure in which a hole 88 extending in the axial direction is provided instead of the groove.

Figure 21:
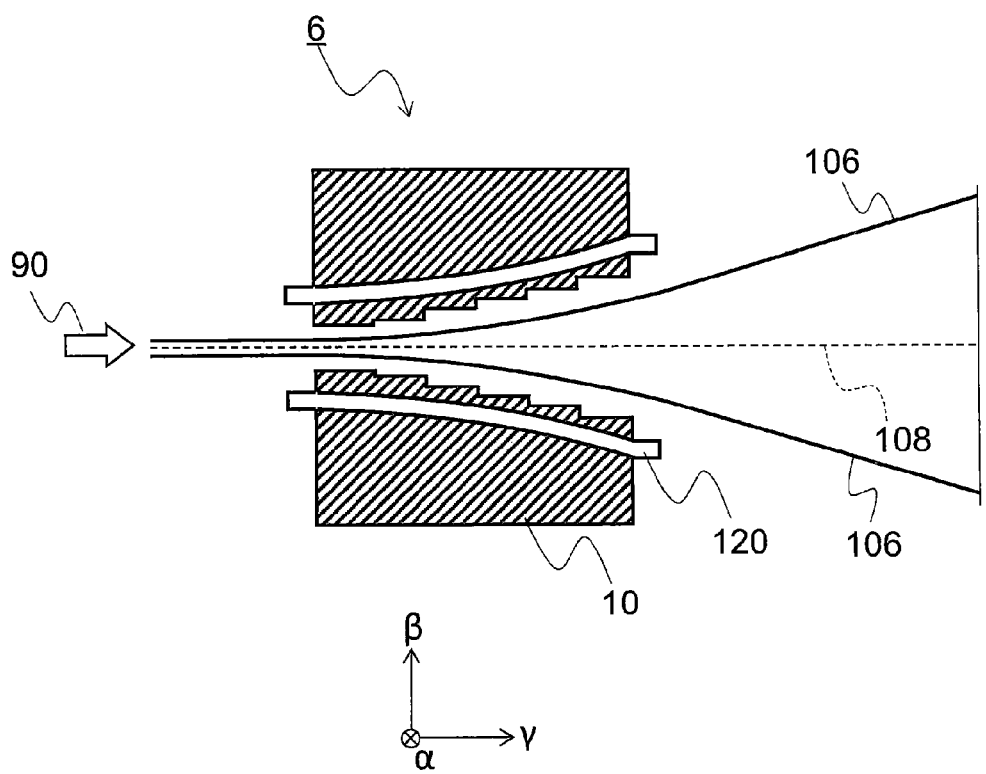
FIG. 21 is a cross-sectional view when the scanning magnet is taken along a plane passing through a central axis.

FIG. 21 illustrates a scanning magnet 6 according to a fourth embodiment of the present invention. FIG. 21 schematically illustrates a cross-sectional view of the scanning magnet 6 taken along a plane passing through the central axis. An outer peripheral surface 106 (beam-passing-region outer peripheral surface 106) of a region through which the charged particle beam 90 passes when scanning is performed with the maximum kick amount is indicated by a solid line. Further, a trajectory 108 of a charged particle beam 90 when the kick amount is set to 0 is indicated by a broken line. The inner wall of a yoke 10 of the scanning magnet 6 has a shape corresponding to the beam-passing-region outer peripheral surface 106. When the inner diameter being the diameter of a circle passing through the distal end of each tooth, and the outer diameter being the diameter of a circle passing through the deepest portion of each groove are defined, the inner diameter and the outer diameter of the yoke 10 become smaller toward the upstream side, and the inner diameter and the outer diameter of the yoke 10 become larger toward the downstream side.

The internal space of the yoke 10, that is, the columnar space has a side surface that expands outward toward the downstream side along the trajectory of the deflecting charged particle beam 90. The forward section and the backward section of each winding 120 are warped outward from the central axis direction toward the downstream side along the side surface of the columnar space.

According to such a structure, in comparison to the case where the inner diameter and the outer diameter are constant from the upstream side to the downstream side, the region where the magnetic flux density is to be generated is narrowed, and the excitation current flowing through each winding is reduced. Thus, the drive circuit that controls the current flowing through each winding becomes small.

Figure 22:
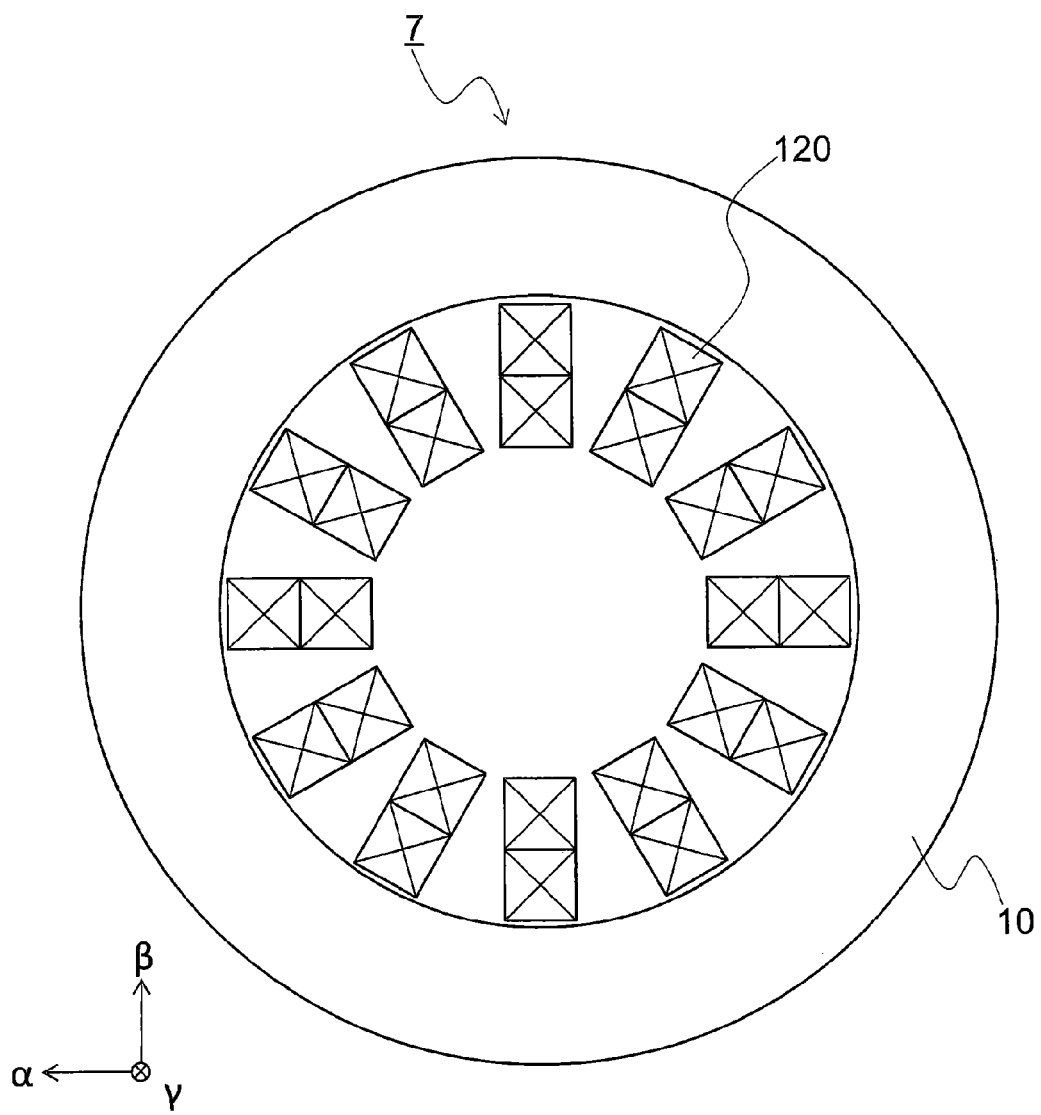
FIG. 22 is a diagram schematically illustrating a cross-sectional shape of a scanning magnet.

FIG. 22 illustrates a scanning magnet 7 according to a fifth embodiment of the present invention. A yoke 10 of the scanning magnet 7 according to the present embodiment is not provided with grooves and teeth, and each winding 120 is disposed on the inner wall surface of the yoke 10. Therefore, it is possible to cause each winding 120 to have a structure of widening in the circumferential direction, and the flatness of the magnetic flux density is improved. Furthermore, the change in the flatness when the scan angle θ is changed is reduced.

The present invention is not limited to the above embodiments, and includes various modification examples. Each of the above embodiments is provided for describing the present invention in an easy-to-understand manner, and the present invention is not necessarily limited to those having all the configurations described.

Further, a portion of the configuration of one embodiment may be replaced with the configuration of another embodiment, and the configuration of one embodiment may be added to the configuration of another embodiment. Furthermore, a portion of the configuration of each embodiment may be added to, deleted from, or replaced with another configuration.

In the above description, the discrete spot scanning irradiation method of stopping the current flowing through each winding between the irradiation spots has been described, but a continuous spot irradiation method of not stopping the current flowing through each winding between the irradiation spots may be used.

In addition to the synchrotron accelerator 44, various known accelerators such as a cyclotron accelerator and a synchrocyclotron accelerator may be used as the accelerator 40. The charged particles accelerated by the accelerator 40 may be protons, heavy particles such as carbon, or the like.

The scanning magnet according to each embodiment may be provided in the beam transport device 46 or the accelerator 40 in addition to the irradiation nozzle. That is, the scanning magnet according to each embodiment may be used for the purpose of correcting the trajectory of the charged particle beam 90 in the beam transport device 46 or the accelerator 40.

Figure 23:
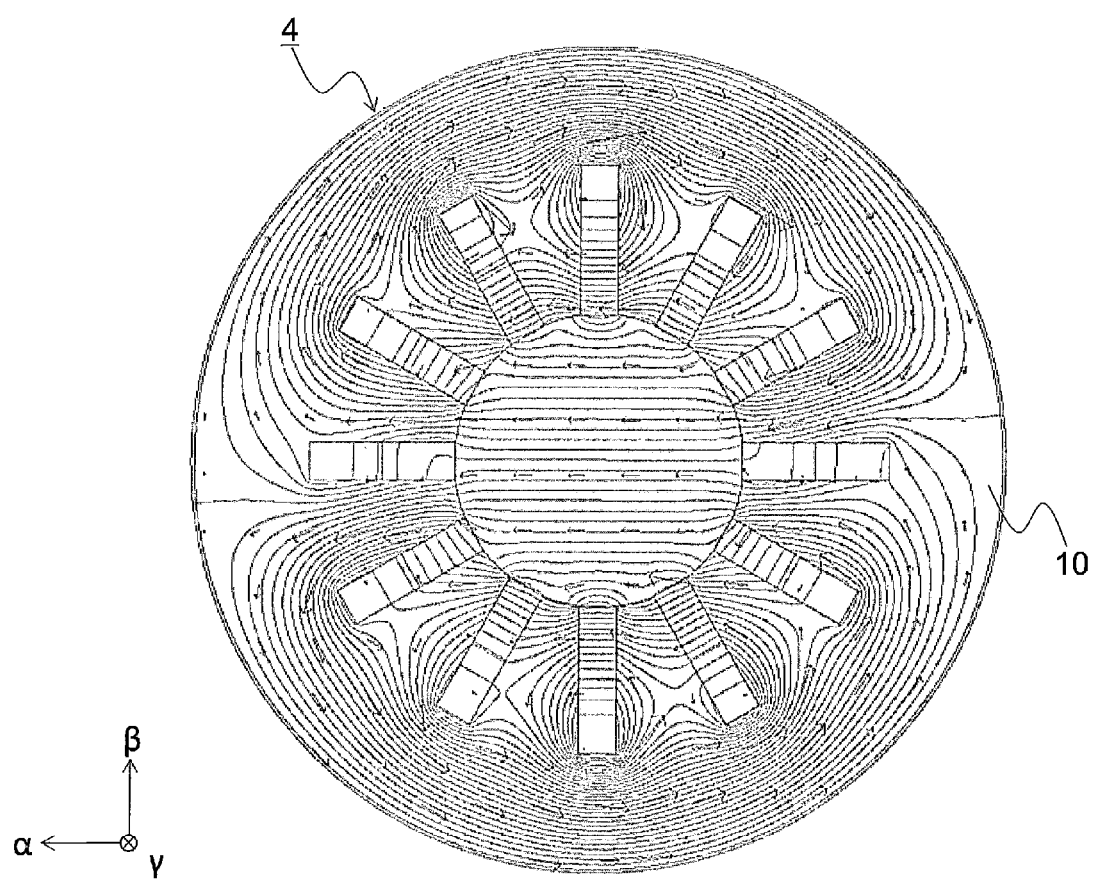
FIG. 23 is a diagram illustrating a simulation result of the scanning magnet.

FIG. 23 illustrates simulation results for the scanning magnet 4 illustrated in FIGS. 15 and 16. In FIG. 23, the distribution of the magnetic flux density when the magnetic flux density in the internal space of the yoke 10 is directed in an α-axis positive direction is indicated by arrows and magnetic force lines.

REFERENCE SIGNS LIST

1, 4, 5, 6, 7 scanning magnet
2, 2A, 2B scanning magnet control system
3 particle therapy system
10 yoke
12 tooth
20 command conversion device
22 scanning magnet control apparatus
24U, 28U winding
U drive circuit
24V, 28V winding
V drive circuit
24W, 28W winding
W drive circuit
26 DC power source
30 drive circuit
32 overall control apparatus
34 accelerator/beam transportation control apparatus
36 irradiation nozzle control apparatus
38 display
40 accelerator
42 injector
44 synchrotron accelerator
46 beam transport device
48 bending magnet
50 irradiation nozzle
52 patient
54 couch
60 target volume
62 dose monitor
64 position monitor
66 ridge filter
68 range shifter
70 dose monitor control apparatus
72 position monitor control apparatus
80 layer irradiated with same energy
82 irradiation spot
88 hole
120 winding

The invention claimed is:

1. A scanning magnet comprising:
a plurality of windings each having a loop path including a forward section and a backward section extending along a trajectory of a charged particle beam, and the windings surrounding a columnar space through which the charged particle beam passes,
wherein the forward section and the backward section in each of the windings are arranged at a predetermined interval along an outer circumferential direction of the columnar space, and
wherein the plurality of windings has a distributed winding structure, in which the forward section or the backward section of one of the plurality of windings is disposed between the forward section and the backward section of each of the other windings, and the forward section or the backward section of each of the other windings is disposed between the forward section and the backward section of the one of the plurality of windings.

2. The scanning magnet according to claim 1, wherein the plurality of windings has a rotationally symmetric structure around an axis of the columnar space.

3. A particle therapy system comprising:
an accelerator;
a beam transport device that transports a charged particle beam extracted from the accelerator; and
an irradiation nozzle for irradiating a patient with the charged particle beam transported by the beam transport device,
wherein at least one of the beam transport device and the irradiation nozzle includes the scanning magnet according to claim 1.

4. The scanning magnet according to claim 1, further comprising:
a yoke surrounding the columnar space; and
a plurality of grooves which are formed in an inner wall of the yoke and extend in an axial direction of the yoke, the plurality of grooves each having the forward section or the backward section of the winding disposed therein,
wherein a distal end portion of a tooth formed between the adjacent grooves is widened in a circumferential direction of the inner wall of the yoke.

5. The scanning magnet according to claim 1, further comprising:
a yoke surrounding the columnar space; and
a plurality of holes which are formed in the yoke and extend in an axial direction of the yoke, the plurality of holes each having the forward section or the backward section of the winding disposed therein.

6. The scanning magnet according to claim 1, further comprising:
a control apparatus that controls a current flowing through each of the windings,
wherein the control apparatus is configured to:
acquire an excitation current target value for each of the plurality of windings, the excitation current target value being obtained when a scan angle in a circumferential direction of the columnar space is given to each of a plurality of periodic functions corresponding to the plurality of windings, and
control a current flowing through each of the windings, based on the excitation current target value acquired for each of the windings.

7. The scanning magnet according to claim 6,
wherein three windings are provided, and
wherein the plurality of periodic functions include three sine functions or cosine functions shifted from each other by 120° on an angle variable axis.

8. The scanning magnet according to claim 1,
wherein the columnar space has a side surface that expands outward toward a downstream side along a trajectory of the deflecting charged particle beam, and
wherein the forward section and the backward section of each of the windings are warped outward from an axial direction, toward the downstream side along the side surface of the columnar space.

9. A scanning magnet comprising:
a plurality of windings each having a forward section and a backward section extending along a trajectory of a charged particle beam, and the windings surrounding a columnar space through which the charged particle beam passes,
wherein the forward section and the backward section in each of the windings are arranged at a predetermined interval along an outer circumferential direction of the columnar space,
wherein the forward section or the backward section of one of the plurality of windings is disposed between the forward section and the backward section of another winding,
wherein the scanning magnet further comprises:
a yoke surrounding the columnar space; and
a plurality of grooves which are formed in an inner wall of the yoke and extend in an axial direction of the yoke, the plurality of grooves each having the forward section or the backward section of the winding disposed therein, and
wherein a distal end portion of a tooth formed between the adjacent grooves is widened in a circumferential direction of the inner wall of the yoke.

10. A scanning magnet comprising:
a plurality of windings each having a forward section and a backward section extending along a trajectory of a charged particle beam, and the windings surrounding a columnar space through which the charged particle beam passes,
wherein the forward section and the backward section in each of the windings are arranged at a predetermined interval along an outer circumferential direction of the columnar space,
wherein the forward section or the backward section of one of the plurality of windings is disposed between the forward section and the backward section of another winding,
wherein the scanning magnet further comprises:
a yoke surrounding the columnar space; and
a plurality of holes which are formed in the yoke and extend in an axial direction of the yoke, the plurality of holes each having the forward section or the backward section of the winding disposed therein.

11. A scanning magnet comprising:
a plurality of windings each having a forward section and a backward section extending along a trajectory of a charged particle beam, and the windings surrounding a columnar space through which the charged particle beam passes,
wherein the forward section and the backward section in each of the windings are arranged at a predetermined interval along an outer circumferential direction of the columnar space,
wherein the forward section or the backward section of one of the plurality of windings is disposed between the forward section and the backward section of another winding,
wherein the scanning magnet further comprises:
a control apparatus that controls a current flowing through each of the windings,
wherein the control apparatus is configured to:
acquire an excitation current target value for each of the plurality of windings, the excitation current target value being obtained when a scan angle in a circumferential direction of the columnar space is given to each of a plurality of periodic functions corresponding to the plurality of windings, and
control a current flowing through each of the windings, based on the excitation current target value acquired for each of the windings.

12. The scanning magnet according to claim 11,
wherein three windings are provided, and
wherein the plurality of periodic functions include three sine functions or cosine functions shifted from each other by 120° on an angle variable axis.

13. A scanning magnet comprising:
a plurality of windings each having a forward section and a backward section extending along a trajectory of a charged particle beam, and the windings surrounding a columnar space through which the charged particle beam passes,
wherein the forward section and the backward section in each of the windings are arranged at a predetermined interval along an outer circumferential direction of the columnar space,
wherein the forward section or the backward section of one of the plurality of windings is disposed between the forward section and the backward section of another winding,
wherein the columnar space has a side surface that expands outward toward a downstream side along a trajectory of the deflecting charged particle beam, and
wherein the forward section and the backward section of each of the windings are warped outward from an axial direction, toward the downstream side along the side surface of the columnar space.

* * * * *